(12) United States Patent
Paul et al.

(10) Patent No.: US 7,326,205 B2
(45) Date of Patent: *Feb. 5, 2008

(54) SURGICAL DEVICE WITH BRUSH ELECTRODE AND METHODS FOR ELECTROSURGICAL TREATMENT

(75) Inventors: Saurav Paul, Minneapolis, MN (US); Kedar Ravindra Belhe, Minnetonka, MN (US); Hong Cao, Shakopee, MN (US); Chou Thao, Brooklyn Park, MN (US)

(73) Assignee: St. Jude Medical, Atrial Fibrillation Division, Inc., Maple Grove, MN (US)

( * ) Notice: Subject to any disclaimer, the term of this patent is extended or adjusted under 35 U.S.C. 154(b) by 295 days.

This patent is subject to a terminal disclaimer.

(21) Appl. No.: 10/856,925

(22) Filed: May 27, 2004

(65) Prior Publication Data

US 2005/0159740 A1  Jul. 21, 2005

Related U.S. Application Data

(63) Continuation-in-part of application No. 10/808,919, filed on Mar. 24, 2004.

(60) Provisional application No. 60/537,092, filed on Jan. 16, 2004.

(51) Int. Cl.
*A61B 18/18* (2006.01)

(52) U.S. Cl. .................................................... 606/41
(58) Field of Classification Search ............ 606/27–52
See application file for complete search history.

(56) References Cited

U.S. PATENT DOCUMENTS

| | | | |
|---|---|---|---|
| 4,358,699 A * | 11/1982 | Wilsdorf | .................. 310/251 |
| 4,415,635 A | 11/1983 | Wilsdorf et al. | |
| 5,676,693 A | 10/1997 | LaFontaine | |
| 6,015,407 A | 1/2000 | Rieb et al. | |
| 6,109,268 A * | 8/2000 | Thapliyal et al. | ............ 128/898 |
| 6,168,594 B1 | 1/2001 | LaFontaine et al. | |
| 6,402,745 B1 | 6/2002 | Wilk | |
| 6,416,514 B1 | 7/2002 | Ein-Gal | |
| 6,780,180 B1 * | 8/2004 | Goble et al. | .................. 606/41 |
| 2001/0024735 A1 | 9/2001 | Kuhlmann-Wilsdorf et al. | |
| 2002/0010463 A1 | 1/2002 | Mulier et al. | |

* cited by examiner

*Primary Examiner*—Michael Peffley
*Assistant Examiner*—Pete Vrettakos
(74) *Attorney, Agent, or Firm*—Heimbecher & Assoc., LLC

(57) ABSTRACT

A surgical device incorporates a brush electrode for tissue ablation and other forms of electrosurgical treatment. A plurality of flexible filaments compose the brush electrode, through which therapeutic energy (e.g., RF energy) is applied to target tissue for the formation of spot or continuous linear lesions, cauterization, incision, and desiccation. A fluid delivery system is used in conjunction with the brush electrode to apply fluid to the filaments and surgical site.

26 Claims, 18 Drawing Sheets

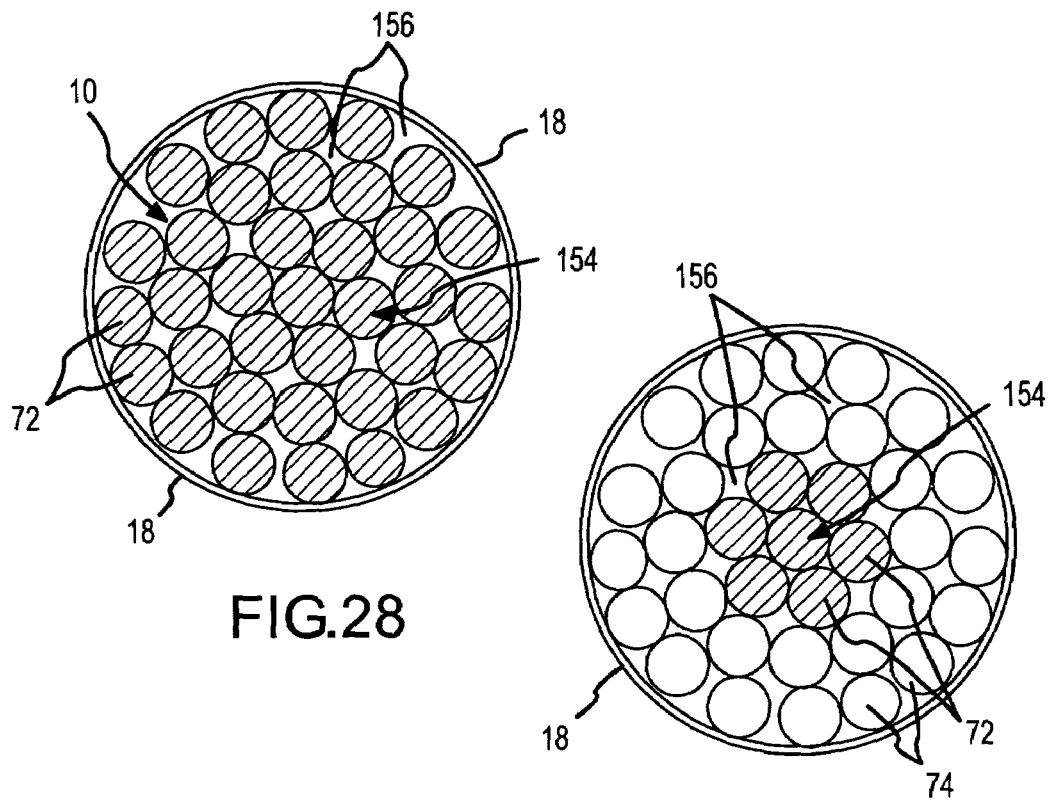
FIG.28
FIG.29
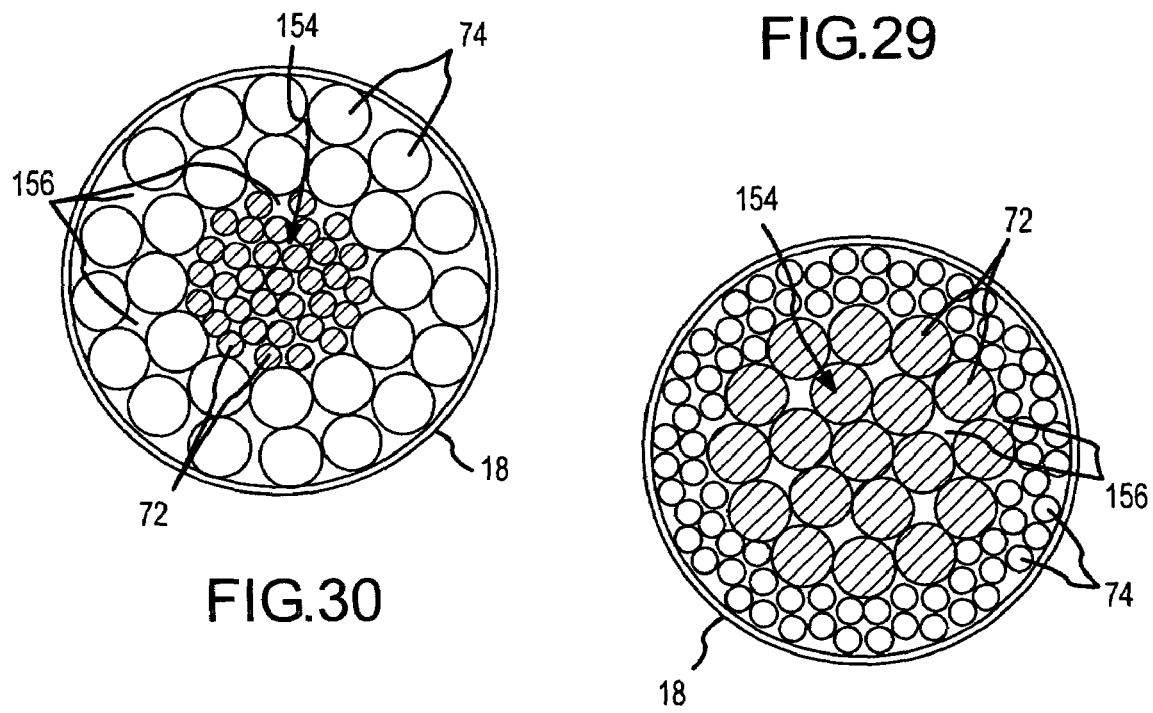
FIG.30
FIG.31

SURGICAL DEVICE WITH BRUSH ELECTRODE AND METHODS FOR ELECTROSURGICAL TREATMENT

CROSS-REFERENCE TO RELATED APPLICATIONS

This application claims priority pursuant to 35 U.S.C. §120 to and is a continuation-in-part of U.S. application Ser. No. 10/808,919 (the '919 application) filed 24 Mar. 2004, entitled Brush Electrode and Method for Ablation, which is hereby incorporated by reference in its entirety as though fully set forth herein. This application also claims priority pursuant to 35 U.S.C. §119(e) to U.S. provisional application No. 60/537,092 (the '092 application) filed 16 Jan. 2004, entitled Brush Electrode and Method for Ablation, which is hereby incorporated by reference in its entirety as though fully set forth herein. This application is related to: U.S. application Ser. No. 10/856,926 (the '926 application) filed May 27, 2004, which is also a continuation-in-part of the '919 application and also claims priority pursuant to 35 U.S.C. §119(e) to the '092 application: and U.S. application Ser. No. 11/190,724 (the '724 application) filed. Jul. 27, 2005, which is a continuation-in-part of each of the '919, '926, and the present application and also claims the benefit of priority to the '092 application.

BACKGROUND OF THE INVENTION a. Field of the Invention

The instant invention is directed toward a surgical device incorporating a brush electrode and methods for using the brush electrode for tissue ablation and other forms of electrosurgical treatment. The brush electrode is composed of a plurality of flexible filaments or bristles for applying therapeutic energy to target tissue for the formation of spot or continuous linear lesions, cauterization incision cutting, and desiccation.

b. Background Art

Surgical devices and techniques utilizing electrodes to transfer therapeutic energy to tissue are well know. Electrosurgery allows for the incision, cauterization, fulguration, and desiccation of tissue through the application of high-power, radio frequency (RF) energy to tissue through an electrode. Ablation techniques, whereby the target tissue is necrotized through coagulation, are also performed using surgical devices with electrodes to transfer RF energy to tissue. Many benefits may be gained by forming lesions in tissue—for example, control of cardiac arrhythmia or tachycardia, removal of skin diseases, or the treatment of varicose veins—if the depth and location of the lesions being formed can be controlled. In particular, it can be desirable to elevate tissue temperature to around 50° C. until lesions are formed via coagulation necrosis, which changes the electrical properties of the tissue. For example, when sufficiently deep lesions are formed at specific locations in cardiac tissue via coagulation necrosis, undesirable ventricular tachycardia may be lessened or eliminated. "Sufficiently deep" lesions means transmural lesions in some cardiac applications.

Several difficulties may be encountered, however, when attempting to form adequately-deep lesions at specific locations using some existing surgical ablation electrodes. For example, when forming lesions with RF energy, high temperature gradients are often encountered in the vicinity of the electrode. At the edges of some existing electrodes are regions of very high current density leading to large temperature gradients and hot spots. These "edge effects" may result in the formation of undesirable coagulum and charring of the surface tissue. For example, undesirable coagulum may begin to form when blood reaches around 80° C. for an appreciable length of time, and undesirable tissue charring and desiccation may be seen when tissue reaches around 100° C. for an appreciable length of time. There two types of undesirable coagulum: coagulum that adheres to and damages the medical device; and coagulum blood clots or curds that may enter a patient's bloodstream, possibly resulting in other health problems for the patient. Charring of the surface tissue may also have deleterious effects on a patient.

As the temperature of the electrode is increased, the contact time required to form an adequately-deep lesion decreases, but the likelihood of charring surface tissue and forming undesirable coagulum increases. As the temperature of the electrode is decreased, the contact time required to form an adequately-deep lesion increases, but the likelihood of charring surface tissue and forming undesirable coagulum decreases. It is, therefore, a balancing act trying to ensure that tissue temperatures are adequately high for long enough to create deep lesions, while still preventing or minimizing coagulum formation and/or charring of the surface tissue. Active temperature control may help, but the placement of thermocouples, for example, is tricky and setting the RF generator for a certain temperature becomes an empirical exercise as actual tissue temperatures are generally different from those recorded next to the electrode due to factors such as convection and instrument design.

Another difficulty encountered with existing electrosurgical and ablation electrodes is assurance of adequate tissue contact. Current techniques for creating continuous linear lesions in epicardial or other applications include, for example, dragging a conventional electrode on the tissue, using an array electrode, or using pre-formed electrodes. All of these devices comprise rigid electrodes that do not always conform to the tissue surface, especially when sharp gradients and undulations are present. Consequently, continuous linear lesions are difficult to achieve on trabecular surfaces. When forming lesions on an epicardial surface of a heart, for example, the beating of the heart further complicates matters, making it difficult to keep adequate contact between the electrode and the tissue for a sufficient length of time to form a desired lesion. With a rigid electrode, it can be quite difficult to maintain sufficient contact pressure until an adequate lesion has been formed. This problem is exacerbated on contoured or trabecular surfaces. If the contact between the electrode and the tissue cannot be properly maintained, a quality lesion is unlikely to be formed.

Ablation devices based upon a virtual electrode may address some of the difficulties, but these devices often require high flow rates of conductive fluid (e.g., typically around 70 milliliters per minute) to maintain effective cooling for high-power, RF applications. The introduction of a large amount of conductive fluid into a patient's bloodstream may have detrimental effects on the patient. Concerns also arise when using present electrosurgical devices, which can undesirably char tissue when used for incision and coagulation purposes during surgery.

Thus, there remains a need for a surgical instrument that address these issues with the existing designs and that permits the formation of uniform spot and continuous linear lesions, including transmural lesions, on smooth or contoured surfaces.

The information included in this background section of the specification, including any references cited herein and any description or discussion thereof, is included for technical reference purposes only and is not to be regarded subject matter by which the scope of the invention is to be bound.

BRIEF SUMMARY OF THE INVENTION

The present invention is a surgical device with a new electrode adaptable for a range of surgical applications including ablation, coagulation, cauterization, incision, fulguration, and desiccation. The invention provides a clinician with the ability to form adequately-deep spot or continuous linear lesions in tissue while reducing the formation of undesirable coagulum and charring of the surface tissue. Alternatively, the invention may be used to create therapeutically desired coagulum, for example, to arrest bleeding or to dissipate varicose veins. This invention also allows a clinician to apply a reasonable amount of therapeutic RF energy, while mitigating electrode-tissue contact problems and/or reducing the amount of conductive fluid (e.g., isotonic saline) possibly entering a patient's bloodstream during the procedure.

In one embodiment of the invention, an electrosurgical device incorporates a brush electrode that facilitates electrode-tissue contact in target tissue. The brush electrode is composed of a plurality of flexible filaments adapted to transfer therapeutic energy to target tissue. The device also incorporates a conductor operatively connected with and adapted to transfer the therapeutic energy to the plurality of flexible filaments. The flexible filaments may have longitudinal axes and be aligned generally parallel to each other with respect to their longitudinal axes. The flexible filaments may also define interstitial spaces between and among the filaments where the interstitial spaces are adapted to direct fluid predominantly parallel to longitudinal axes of the flexible filaments. The electrosurgical device may further have a fluid-delivery means adapted to deliver fluid to the interstitial spaces.

In another embodiment, the invention is embodied in a surgical pencil for surgical treatment of tissue. The surgical pencil is composed of a shaft with a distal end, a brush electrode, a conductor, and an attachment means for securing the brush electrode to the distal end of the shaft. The brush electrode is composed of a plurality of flexible filaments adapted to transfer therapeutic energy to target tissue. The flexible filaments extend from the distal end of the shaft. The conductor is in electrical contact with the plurality of flexible filaments. The shaft may further define a lumen adapted to carry a fluid from a fluid source to said brush electrode.

In a further embodiment of the invention, an surgical device for transferring therapeutic energy to tissue is disclosed. The surgical device is composed of a shaft having a distal end, a brush electrode adapted to apply therapeutic energy to target tissue, and a conductor. The brush electrode is further composed of an embedded portion and an exposed portion, wherein the exposed portion has a distal end, and a working surface at the distal end of the exposed portion. The exposed portion extends from the distal end of the shaft. The conductor is in direct electrical contact with the brush electrode and is adapted to carry the therapeutic energy to the brush electrode. The surgical device may further have an energy source for generating the therapeutic energy, wherein the energy source is electrically coupled with the conductor. In one configuration, the shaft may further define a shaft lumen and the surgical device may have a fluid pump fluidically coupled with a reservoir of fluid. The fluid pump may be fluidically coupled with the shaft lumen, whereby the fluid may be delivered to the working surface of the exposed portion of the brush electrode. The surgical device of may further have an introducing cannula defining a lumen, wherein an inner diameter of the lumen is greater than an outer diameter of the shaft and the shaft operably resides within the lumen.

In yet another embodiment of the invention, a surgical device may be formed by an outer shaft with a distal end, an inner sheath with a distal end, a brush electrode, a conductor, and a flexible boot at the distal end of the outer shaft. An annular channel may be defined between the outer shaft and the inner sheath, wherein the annular channel is adapted to carry fluid. The brush electrode may be supported by a mechanical interface, which in turn may be supported, at least in part, by the distal end of the inner sheath. The brush electrode may be composed of an embedded portion and an exposed portion, wherein the exposed portion extends from the distal end of the outer shaft and comprises a working surface. The conductor, composed of an uninsulated portion in electrical contact with the brush electrode, is adapted to carry therapeutic energy from an energy source to the brush electrode. The brush electrode is adapted to then apply the therapeutic energy to target tissue. The flexible boot defines an annular fluid jacket around a booted portion of the brush electrode, which includes at least a portion of the exposed portion of the brush electrode. The annular fluid jacket is adapted to carry fluid that is in fluid communication with said annular channel.

Other features, details, utilities, and advantages of the present invention will be apparent from the following more particular written description of various embodiments of the invention as further illustrated in the accompanying drawings and defined in the appended claims.

BRIEF DESCRIPTION OF THE DRAWINGS

FIGS. 28-35 depict different cross-sectional configurations for brush electrodes according to the present invention.

DETAILED DESCRIPTION OF THE INVENTION

Several embodiments of a surgical device 2 with a brush electrode 10 according to the present invention are depicted in the figures. As described further below, the brush electrode 10 of the present invention provides a number of advantages, including, for example, the formation of deep lesions in tissue while reducing the formation of undesirable charring of the surface tissue, the application of therapeutic RF energy for surgical effects at a reasonable and manageable level, the achievement of greater electrode-tissue contact, and the mitigation of electrode-tissue contact problems. The present invention facilitates the formation of a deep lesion or incision in a shorter period of time than required by other ablation or electrosurgical devices. It also provides the ability to create lesions in highly perfused tissue or in fluid-rich environments. The brush electrode 10 facilitates enhanced tissue contact in difficult environments (e.g., during ablation of a contoured or trabecular tissue surface on a beating heart) by readily conforming to surface contours. Depending upon the power and waveform of the RF energy applied and the configuration of the distal tip of the brush electrode 10, a number of desirable surgical treatments can be provided including ablation, coagulation, cauterization, incision, fulguration, and desiccation.

Figure 1A:
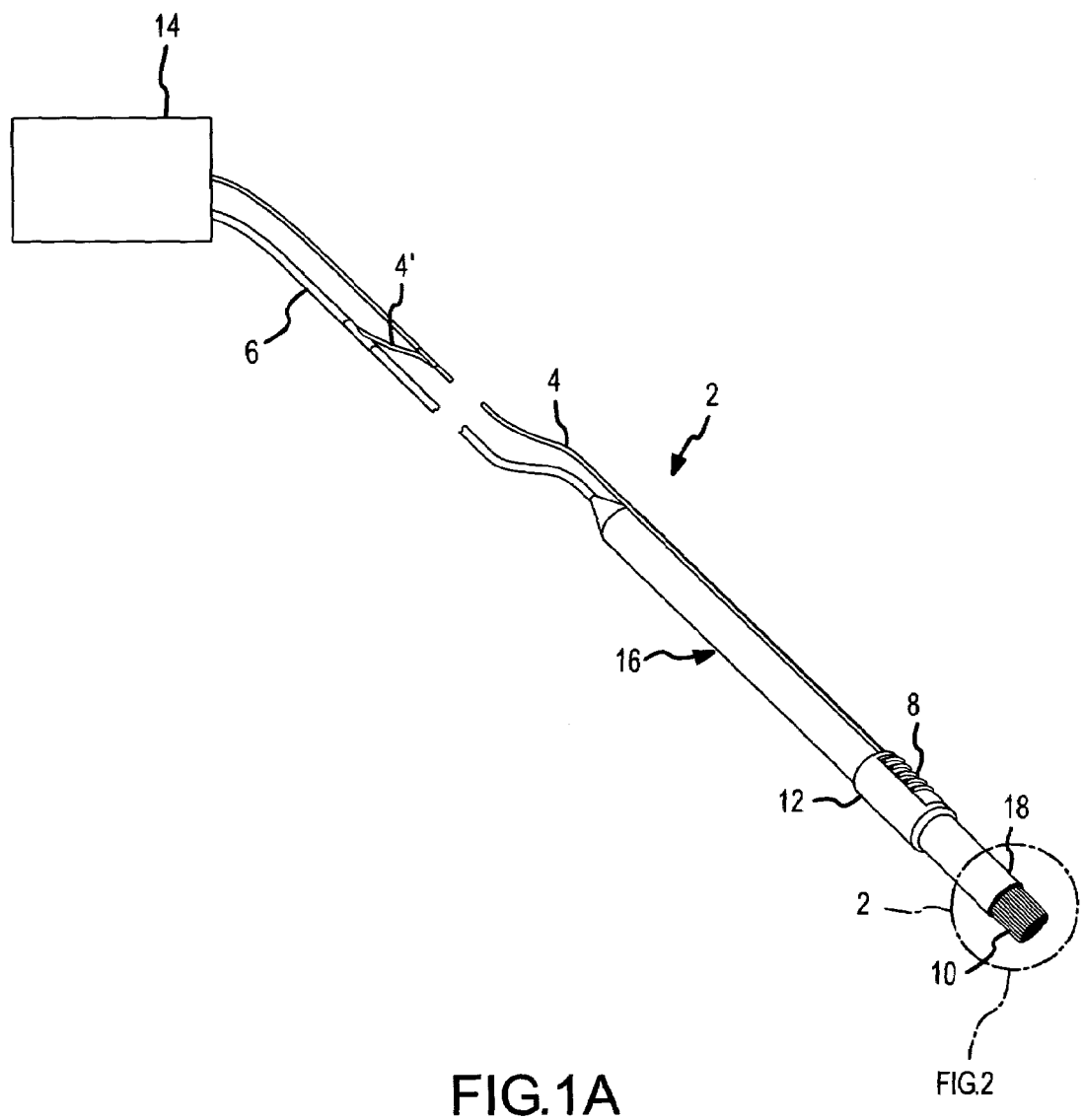
FIGS. 1A-1C are isometric view of several embodiments of a surgical device in the form of a surgical pencil having a brush electrode according to the present invention with differing control features.

FIG. 1A is an isometric view of one embodiment of a surgical device 2 according to the present invention in the form of a surgical pencil 16 and a base unit 14. As depicted in FIG. 1A, the surgical pencil 16 is composed of a handle 12, a pencil shaft 18, and a brush electrode 10. The surgical pencil 16 may be connected to the base unit 14 via a control wire 4 and a fluid conduit 6. The handle 12 may have a switch 8 (or multiple switches or other controllers) coupled with the control wire 4 for controlling function of the surgical pencil 16, the base unit 14, or both. The surgical pencil 16 may also be connected with the base unit 14 via a fluid conduit 6, which may provide conductive or nonconductive fluid to the brush electrode 10 for augmentation of surgical or ablative applications.

Figure 1B:
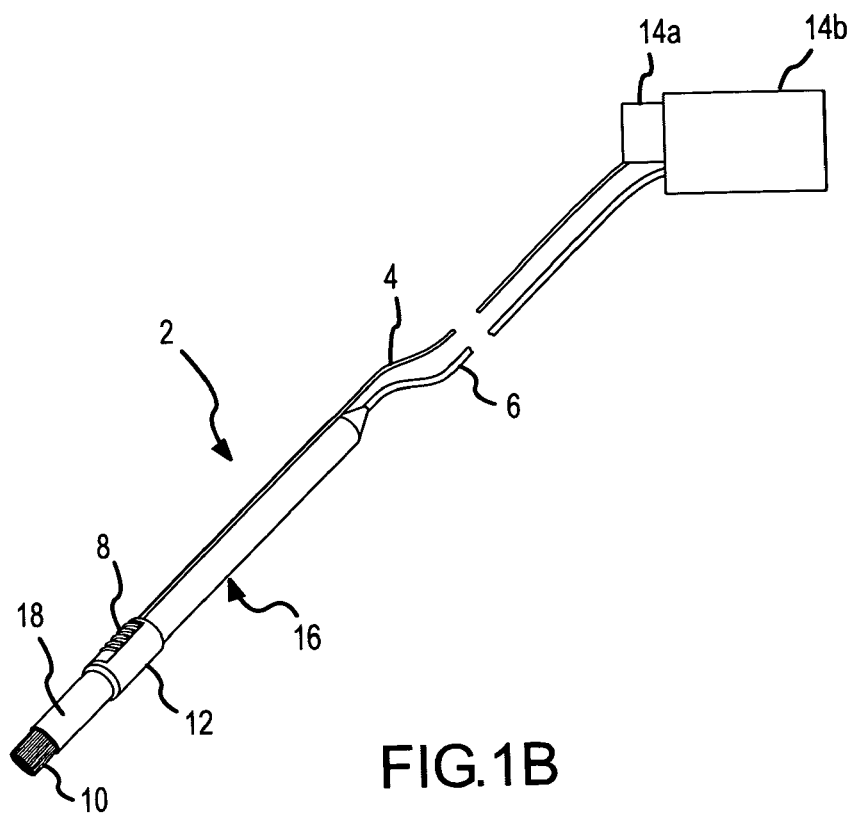
Figure 1C:
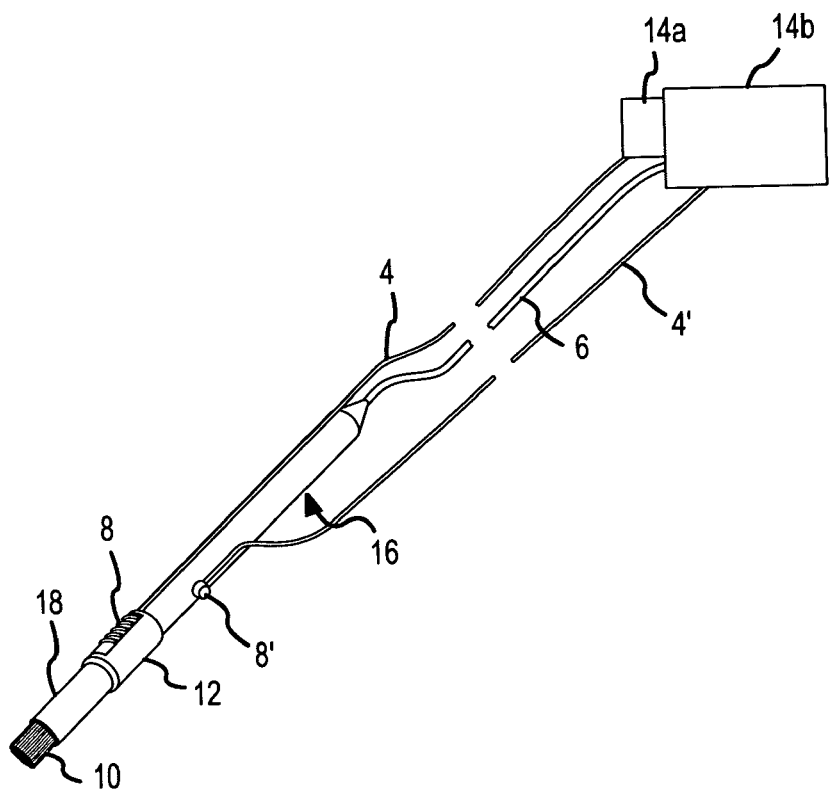
Figure 6:
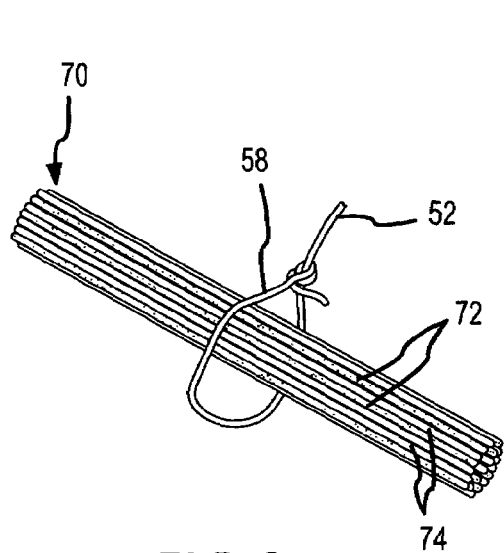
FIGS. 6 and 7 depict steps that may be used to form the brush electrode depicted in, for example, FIG. 5.

The base unit 14 may contain an energy source, for example, an RF generator, and controls to regulate the frequency, power, and duration of the application of such therapeutic energy. The base unit 14 may also house a pump mechanism and a fluid reservoir for introducing fluid to the brush electrode 10. In other embodiments, for example, as depicted in FIGS. 1B and 1C, an energy source 14a may be a separate unit than the fluid pump 14b and reservoir. As shown in FIG. 1C, control of the energy source 14a may be provided by the switch 8 while control of the fluid pump 14b is assigned to a second switch 8'. The switches 8, 8' may be a simple as power switches for actuating and de-actuating the energy source 14a and the fluid pump 14b. Alternatively, the switches 8, 8' may provide higher levels of control through either analog or digital switching technology (e.g., an analog or digital rheostat or potentiometer), allowing the switches 8, 8' to control power levels and flow rates. The control wire 4 may also be a bundle of wires for both controlling and transmitting RF or other therapeutic energy to the surgical pencil 16. Similarly, the fluid conduit 6 may also house a control wire 4', as shown in FIG. 6, for controlling fluid delivery to the surgical pencil 16. Although the pencil shaft 18 depicted in FIGS. 1A-1C has a circular cross section, the cross-section of the pencil shaft 18 may be other than circular.

As also shown in FIGS. 1A-5, the brush electrode 10 is provided at a distal end 24 of the pencil shaft 18. (As used herein, "proximal" refers to a direction away from the body of a patient and toward the clinician. In contrast, "distal" as used herein refers to a direction toward the body of a patient and away from the clinician.) The brush electrode 10 is composed of a plurality of filaments 26 arranged longitudinally in a bundle. As shown particularly in FIG. 5, the bundle of filaments 26 is partially inserted into a lumen 44 defined by the pencil shaft 18 at the distal end of the pencil shaft 18. That portion of the filaments 26 within the lumen 44 may be referred to as an embedded portion 22, and that portion of the filaments extending from the distal end 24 of the pencil shaft 18 may be referred to as an exposed portion 20. The exposed portion 20 of the brush electrode 10 may project a few millimeters from the distal end 24 of the pencil shaft 18. The distance that the exposed portion 20 of the brush electrode 10 extends from the distal end 24 of the pencil shaft 18 varies depending upon a number of factors including the composition of the filaments 26 comprising the brush electrode 10 and the particular area to be treated with the brush electrode 10. As explained further below, the flexible brush electrode 10 provides enhanced tissue contact, particularly for use on contoured or trabecular surfaces.

Figure 2:
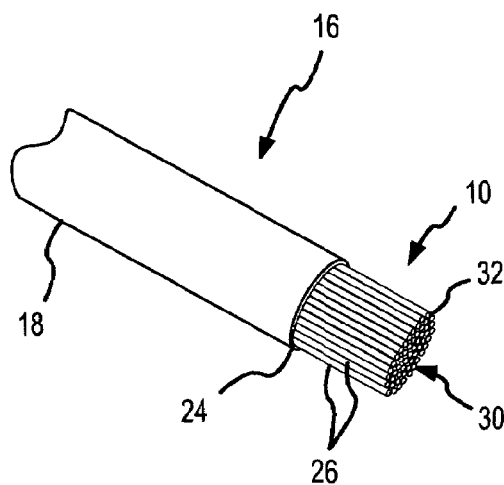
FIG. 2 is an enlarged view of the distal end of the surgical device of FIG. 1A.

FIG. 2 is an enlarged view of the circled region of FIG. 1A. As clearly shown in FIG. 2, the brush electrode 10 according to this embodiment has a relatively flat working surface 30 at the distal tip 32 of the brush electrode 10. In other words, in this depicted embodiment, each of the filaments 26 in the exposed portion 20 extend approximately the same distance from the distal end 24 of the pencil shaft 18. Thus, the distal tip 32 of the brush electrode 10 provides a relatively flat working surface 30 composed of the longitudinal ends of the filaments 26. The pencil shaft 18 of the surgical pencil 16 provides mechanical support for the filaments 26 and may also provide electrical shielding.

The brush electrode 10 may be composed of a bundle of bristles or filaments 26 that each may be constructed from a variety of different materials. Such materials may include nonconductive materials, semi-conductive materials, and conductive materials. For example, the filaments 26 may be formed from metal fibers, metal plated fibers, carbon compound fibers, and other natural materials. Very thin carbon fibers may be used, or relatively thicker, but less conductive, Thunderon® acrylic fibers (Nihon Sanmo Dyeing Company Ltd. of Kyoto, Japan) may be used for the brush electrode filaments 26. Nylon fibers coated with conductive material may also be used. Filaments 26 constructed from metal plated fibers, for example, coated nylon fibers, may have flattened areas around their outer surfaces, resulting in the filaments 26 having noncircular cross-sectional shapes. The filaments 26 may be insulated from each other, or they may be in electrical contact with each other. As explained further below, conductive or nonconductive fluids 34 may flow interstitially within the filaments 26 themselves (see, e.g., FIG. 5) or along the outer surface of the filaments (see, e.g., FIG. 26).

Figure 3:
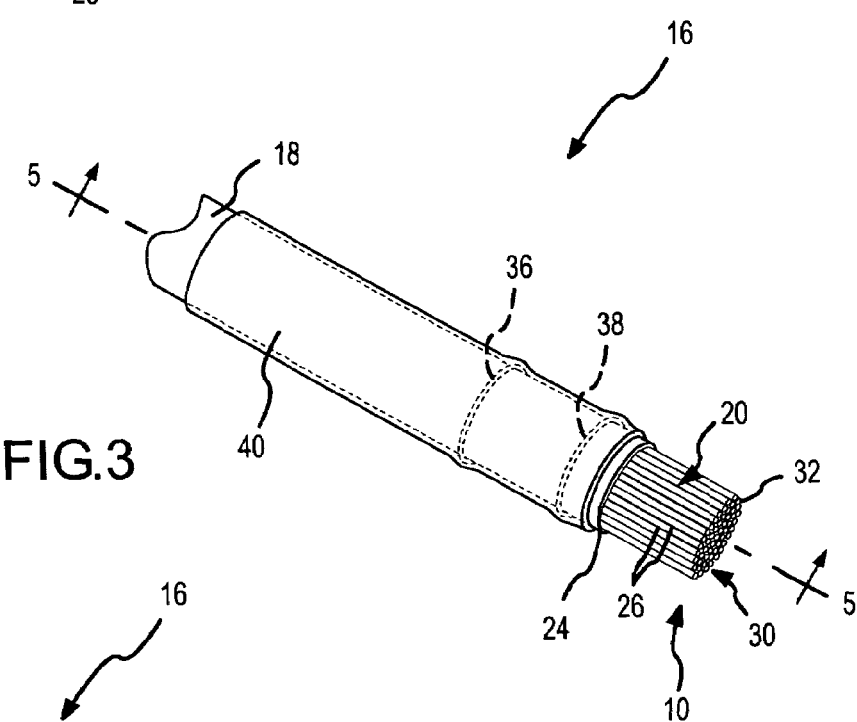
FIG. 3 is similar to FIG. 2, but depicts an alternative embodiment where the brush electrode is secured at the distal end of the surgical pencil by at least one suture that is covered by a section of shrink tube.
Figure 4:
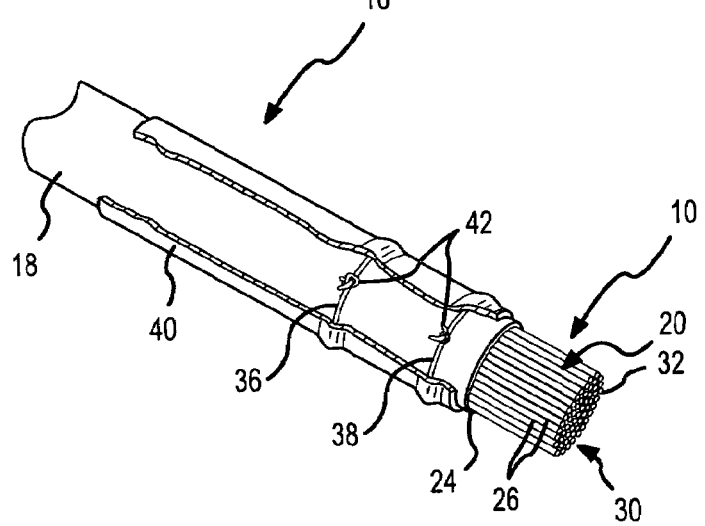
FIG. 4 is similar to FIG. 3, but a portion of the shrink tube has been removed to reveal two sutures attaching the brush electrode to the shaft of the surgical pencil.
Figure 5:
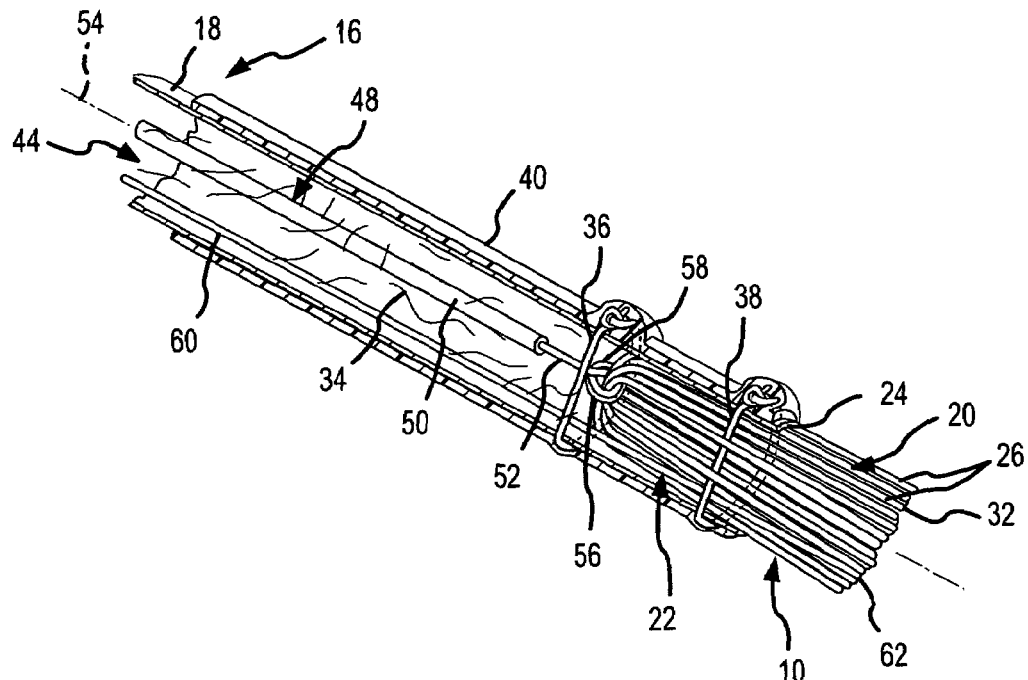
FIG. 5 is an isometric, cross-sectional view of the catheter depicted in FIGS. 3 and 4, taken along line 5-5 of FIG. 3, revealing a primary conductor making electrical contact with a bundle of filaments comprising the brush electrode, and depicting a secondary lead (e.g., for a thermocouple) extending adjacent to the primary conductor and becoming embedded within the brush filaments.

Once the distance that the filaments 26 extend from the distal end 24 of the other sheath 18 is set to a desired length, the bundle of filaments 26 comprising the brush electrode 10 may be fixed to the pencil shaft 18. FIGS. 3-5 depict one technique for fixing or anchoring the brush electrode 10 relative to the pencil shaft 18 using sutures 36, 38. In FIG. 3, a proximal suture 36 and a distal suture 38 are shown in phantom under a section of shrink tube 40 surrounding the outer surface of the pencil shaft 18. The shrink tube 40 protects the sutures 36, 38 mitigating possible snags that may occur due to the presence of the sutures 36, 38, and makes it easier to manipulate the surgical pencil 16. FIG. 4 is similar to FIG. 3, but depicts a portion of the shrink tube 40 broken away to reveal a portion of the two sutures 36, 38. The suture knots 42 are clearly visible in FIG. 4.

FIG. 5 is an isometric, cross-sectional view of the pencil shaft 18 depicted in FIGS. 3 and 4, taken along line 5-5 of FIG. 3. The proximal suture 36 may be used to set the insertion depth of the embedded portion 22 of the brush electrode 10 in the distal end 24 of the pencil shaft 18. In this figure, the distal suture 38 pierces the embedded portion 22 of the filaments 26 and thereby restricts movement of the brush electrode 10 relative to the pencil shaft 18 of the surgical pencil 16. In the embodiment depicted in FIG. 5, conductive fluid 34 is shown flowing through the lumen 44 of the pencil shaft 18 from a fluid source (e.g., a pump and reservoir in the base unit 14) to the brush electrode 10. When the conductive fluid 34 flows through the brush electrode 10, it creates a wet-brush electrode in which impinging jets of fluid traveling interstitially impact the tissue 46 (see, e.g., FIGS. 38-40) at the tissue-electrode interface, which makes it easier to control temperature rises at the interface. Wet-brush electrodes are discussed further below. In an alternative embodiment, the lumen 44 depicted in FIG. 5 may comprise a plurality of separate lumen.

Figure 7:
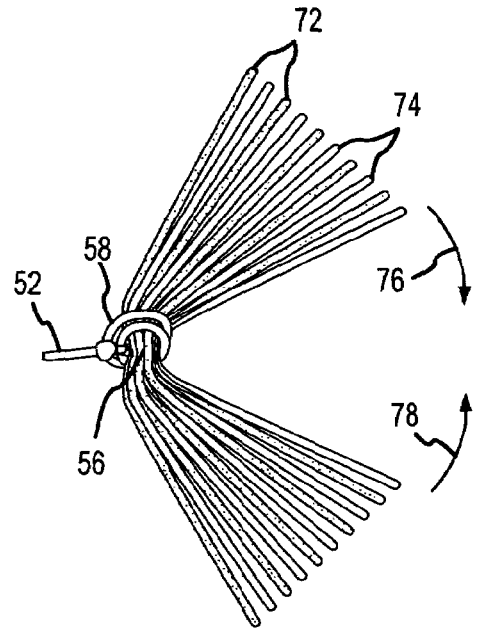

FIG. 5 also clearly depicts a primary conductor 48 having an insulated portion 50 and an uninsulated portion 52. The primary conductor 48 carries RF energy from an energy source in the base unit 14 to the brush electrode 10. As depicted in FIG. 5, the primary conductor 48 extends within the fluid-carrying lumen 44 of the surgical pencil 16, along a longitudinal axis 54 of the surgical pencil 16. The primary conductor 48 may comprise, for example, insulated copper wire with an uninsulated portion 52 in electrical contact with the brush electrode 10. In this embodiment, the uninsulated portion 52 of the primary conductor 48 is looped or noosed around the filaments 26 comprising the brush electrode 10 at a connection point 56 (FIG. 7). At the loop or noose 58, RF energy is transferred from the primary conductor 48 to the conductive filaments 26 of the brush electrode 10. In this embodiment, the uninsulated portion 52 of the primary conductor 48 is connected with the embedded portion 22 of the brush electrode 10 so that the connection between the primary conductor 48 and the brush electrode 10 is protected within the pencil shaft 18 of the surgical pencil 16.

Also clearly visible in FIG. 5 is an embedded or secondary lead 60, which extends substantially parallel to the primary conductor 48. A distal end 62 of the secondary lead 60 becomes embedded with the filaments 26 of the brush electrode 10. As discussed further below in connection with, for example, FIG. 37, the secondary lead 60, when present, may be operatively connected to some type of sensor embedded in the brush electrode 10 (e.g., a thermal sensor 64, an ultrasound sensor 66, or a pressure sensor 68). The brush electrode 10 depicted in FIG. 5 acts as a surface-cooled electrode 10.

FIGS. 6 and 7 depict possible steps for forming the brush electrode 10 depicted in FIGS. 1-5. In FIG. 6, a bundle 70 of conductive filaments 72 and nonconductive filaments 74 is formed by using the uninsulated portion 52 of the primary conductor 48 to bind or tie together the filaments 70. In FIG. 6, the uninsulated portion 52 forms a noose around the bundle of filaments 70, but is not yet tightened or snugged against the bundle 70. In FIG. 7, the uninsulated portion 52 of the primary conductor 48 is snuggly noosed around the connection point 56 at approximately the mid-section of the bundle of filaments 70 that will ultimately form the brush electrode 10. The conductive filaments 72 and the nonconductive filaments 74 are then bent around the connection point 56 in the direction of the arrows 76, 78 depicted in FIG. 7. Once the filaments 70 are folded upon themselves about the connection point 56, they are inserted into the distal end 24 of the pencil shaft 18 and positioned relative to the distal end 24 of the pencil shaft 18 so that the desired amount of the filaments 70 extends from the distal end 24 of the pencil shaft 18 and forms the exposed portion 20 of the brush electrode 10. The ends of the filaments 70 may then be trimmed, if desired, to create a desired shape for the working surface 30 at the distal end 32 of the brush electrode 10 (see, e.g., FIGS. 11-14).

Figure 8:
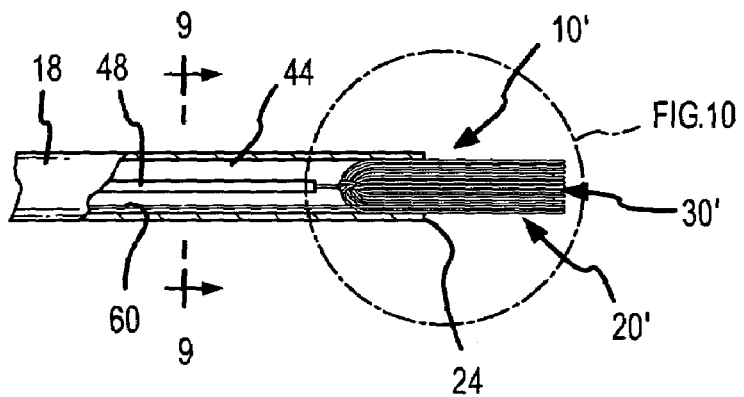
FIG. 8 is similar to FIG. 5, but is a cross-sectional view of an alternative embodiment of the brush electrode, wherein conductive filaments are interspersed among relatively longer nonconductive filaments.
Figure 9:
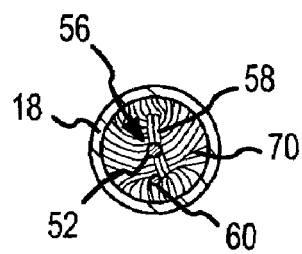
FIG. 9 is a cross-sectional view taken along line 9-9 of FIG. 8.
Figure 10:
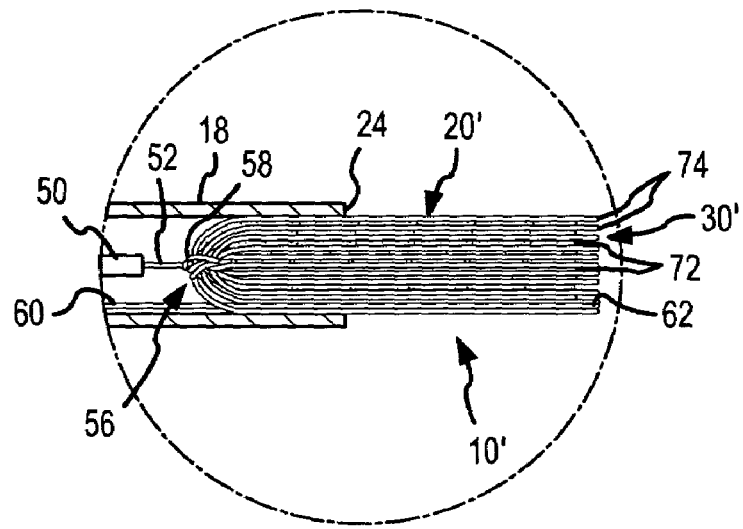
FIG. 10 is an enlarged view of the circled region of FIG. 8.

FIGS. 8, 9, and 10 depict an alternative embodiment of the brush electrode 10'. This standoff brush electrode 10' includes an exposed portion 20' with a working surface 30', wherein the longitudinal ends of the conductive filaments 72 are not flush with the longitudinal ends of the nonconductive filaments 74. As shown to better advantage in FIG. 10, which is an enlarged view of the circled region of FIG. 8, in this alternative embodiment of the brush electrode 10', the conductive filaments 72 are interspersed among relatively longer nonconductive filaments 74. The relatively longer nonconductive filaments 74 prevent the conductive filaments 72 from directly touching the tissue 46 (see, e.g., FIG. 38) when the working surface 30' of the brush electrode 10' is placed normal to the tissue 46 being treated. With this brush electrode 10' configuration and substantially perpendicular orientation of the working surface 30' relative to the tissue 46 being treated, the brush electrode 10' acts as a virtual electrode. If the perpendicular orientation can be maintained, there is no direct contact between the conductive filaments 72 and the tissue 46, and the conductive fluid 34 (see FIG. 5) flowing through the lumen 44 of the pencil shaft 18 makes the electrical contact at the brush-tissue interface. Although FIGS. 8 and 10 depict each of the conductive filaments 72 as being shorter than each of the nonconductive filaments 74, the electrical characteristics of the brush electrode 10' may be adjusted by having some conductive filaments 72 extend to the working surface 30' at the tip of the brush electrode 10', if desired.

FIG. 9 is a cross-sectional view taken along line 9-9 of FIG. 8 and clearly depicts the bundled filaments 70 at the connection point 56 between the filaments 70 and the uninsulated portion 52 of the primary conductor 48. The secondary lead 60 is also visible in FIG. 9. In this embodiment, it is possible to adjust the fluid and electrical contact at the brush-tissue interface through appropriate selection of the conductive and nonconductive filaments 72, 74. Since this configuration of the brush electrode 10' performs most effectively when placed normal or perpendicular to the tissue 46, a relatively short exposed portion 20' for the brush electrode 10' may be desirable with relatively stiff filaments (e.g., Thunderon® filaments).

Figure 11:
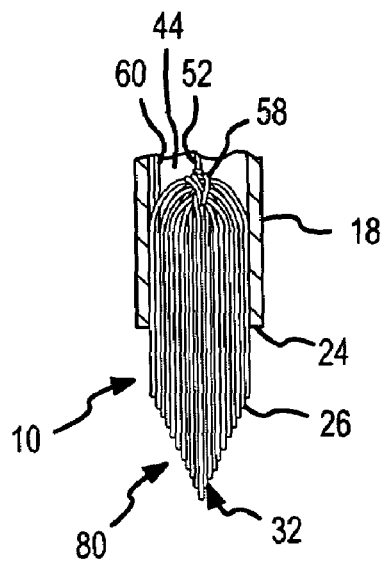
FIGS. 11-14 depict alternative shapes of the bundle of filaments at the tip of the brush electrode.
Figure 12:
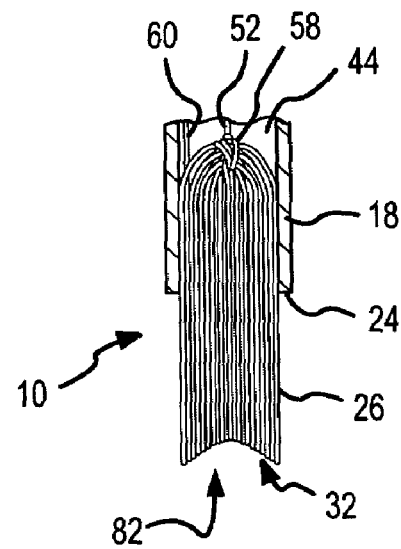
Figure 13:
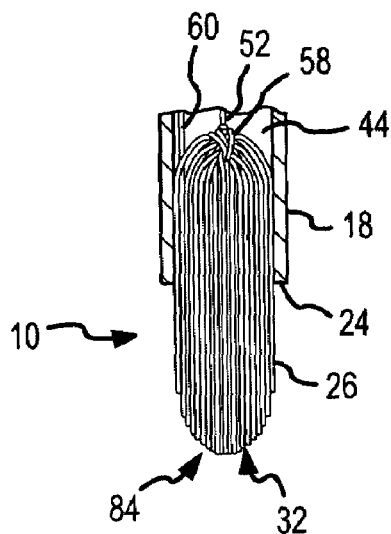
Figure 14:
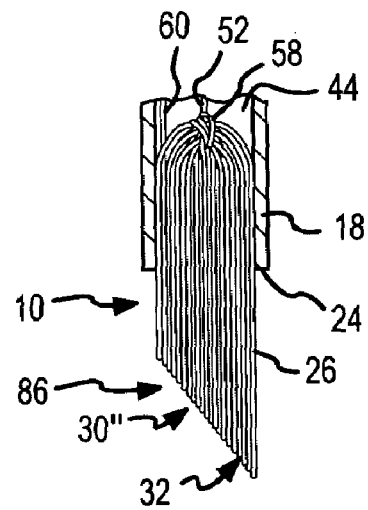

FIGS. 11-14 depict alternative shapes for the filaments 26 comprising the distal tip 32 of the brush electrode 10. The various tip configurations may provide advantages for special applications of brush electrodes 10. FIG. 11 depicts a triangular distal tip 80 with filaments on opposing sides cut at corresponding angles to create a blade-like tip. In an alternative embodiment (not shown), the distal tip may be conical with its longest filaments proximal to the longitudinal axis 54 of the surgical pencil 16 (see FIG. 5). These particular configurations may be advantageous for point applications of therapeutic energy, or for creating an incision in the tissue. In FIG. 12, the working surface of the electrode tip has a concave portion or channel 82. The concave-tip embodiment depicted in FIG. 12 is beneficial for wrap-around applications and provides advantages when treating curved surfaces like the outer surface of a blood vessel. FIG. 13 depicts an arched tip 84. The tip may be similarly a convex or domed tip. This particular configuration is beneficial, for example, when reaching into troughs or depressions on a contoured surface. In an alternative embodiment (not shown), the distal tip 32 may be bowl-shaped, wherein the filaments 26 about the perimeter of the brush electrode 10 are longer than the filaments 26 proximal to the longitudinal axis 54 of the surgical pencil 16. In FIG. 14, the brush electrode 10 has a wedge-shaped tip 86. The wedge-shaped tip 86 facilitates angular placement and increases the area of the working surface 30". The brush electrodes 10 are depicted in many of the drawings with circular cross sections, but may have different cross-sectional configurations.

Figure 15:
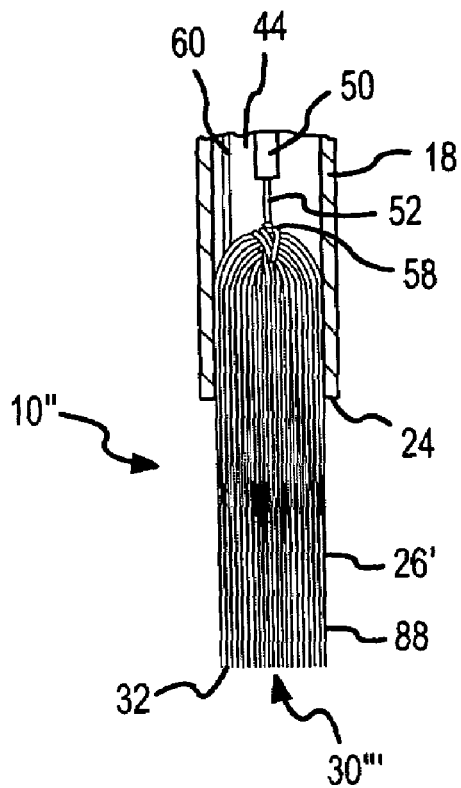
FIG. 15 depicts an alternative embodiment of the filaments of the brush electrode, wherein the individual filaments gradually taper toward their distal ends.

FIG. 15 depicts an example of a brush electrode 10" having continuously varying conductivity along the longitudinal axes of the filaments 26'. In particular, the brush electrode 10" comprises tapered filaments 26'. In this alternative embodiment, the individual filaments 26' of the brush electrode 10", or a portion thereof, have a tapered portion 88 gradually formed toward their distal ends at the distal tip 32 of the brush electrode 10". In other words, at the distal end 24 of the pencil shaft 18, the filaments 26' have larger cross-sectional areas than they have at the distal tip 32, adjacent to the working surface 30''' of the brush electrode 10". The filaments 26' are thus more conductive adjacent to the distal end 24 of the pencil shaft 18 and less conductive along the tapered portion 88 due to the reduction in cross-sectional area. Since the filaments 26' are more conductive adjacent to the distal end 24 of the pencil shaft 18, current flow to the less conductive fluid wetting the brush electrode 10" from the lumen 44 of the pencil shaft 18 is minimized. When less of the RF energy flows into the conductive fluid 34 adjacent to the distal end 24 of the pencil shaft 18, energy transfer into the conductive fluid 34 and the concomitant heating of the conductive fluid 34 before it contacts the surface of the tissue 46 is minimized. Along the tapered portion 88 of the filaments 26' depicted in FIG. 15, the conductivity of the filaments 26' may be matched to the conductivity of the fluid 34 to create a relatively uniform electric field at the brush-tissue interface.

Although not depicted, the tapered portion 88 shown in FIG. 15 could be an inverse taper (i.e., the cross-sectional area of the filaments increases from the distal end 24 of the pencil shaft 18 to the distal tip 32 of the brush electrode), which may be advantageous for certain applications. It should be noted that, in order to vary the conductivity along the length of the filaments, the filaments may also be coated or plated with materials having different or varying electrical conductivity. For example, the filaments, whether tapering or not, could be coated with conductive material. The conductive material coating the filaments in the region most closely adjacent to the distal end 24 of the pencil shaft 18 may be more conductive than the coating on the portion of the filaments most closely adjacent to the distal tip 32 of the filaments themselves. Thus, the conductivity of the filaments would be greater near the distal end 24 of the pencil shaft 18 than near the distal tip 32 of the filaments, even though the cross-sectional areas of the filaments may not change substantially longitudinally along the filaments toward the distal tip 32. Although not specifically shown in the figures, the conductivity of all of the disclosed filaments may also vary radially rather than, or in addition to, varying longitudinally. In other words, the conductivity of the filaments may vary as one moves from the center of the filaments to the surface of the filaments.

Figure 16:
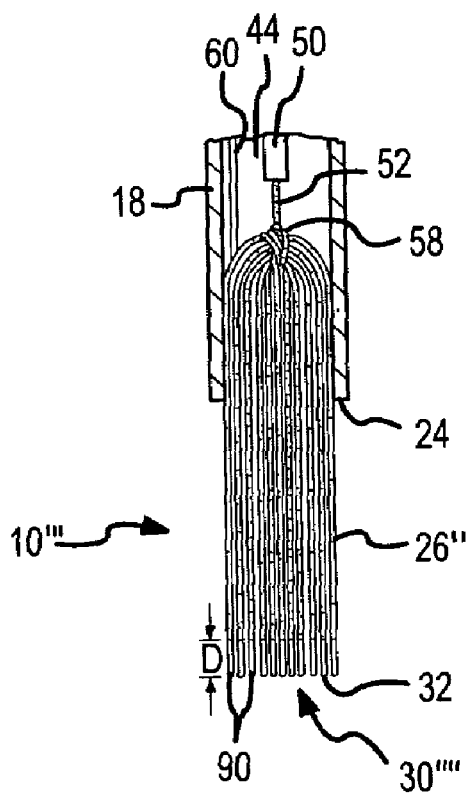
FIG. 16 depicts an alternative embodiment of the filaments of the brush electrode, wherein the individual filaments have nonconductive tips at their distal ends creating a stand-off distance.

FIG. 16 depicts a brush electrode 10''' in which the conductivity of the filaments 26'' varies discontinuously. In particular, FIG. 16 depicts filaments 26'' that are conductive except at their distal ends at the distal tip 32 of the brush electrode 10'''. The distal end of each filament 26'' includes a nonconductive tip 90. These nonconductive tips 90 provide a stand-off distance D when the working surface 30'''' of the brush electrode 10''' is placed substantially perpendicular to the tissue 46 being treated since the conductive portions of the filaments 26'' do not actually touch the tissue 46 in this embodiment. Similar to the embodiment depicted in FIGS. 8-10, the conductive fluid 34 passes through the lumen 44 of the surgical pencil 16 and wet the filaments 26'' of the brush electrode 10'''. The conductive fluid 34 carries the RF energy over the stand-off distance D and to the tissue 46, and thereby acts as a virtual electrode. It should be noted that, although the embodiment depicted in FIG. 16 shows each of the conductive filament 26'' having a nonconductive tip 90, in an alternative embodiment some of the conductive filaments 26'' may extend all the way to the working surface 30'''' of the brush electrode 10''' and thus would, in fact, contact the tissue 46 during use of the brush electrode 10'''.

Figure 17:
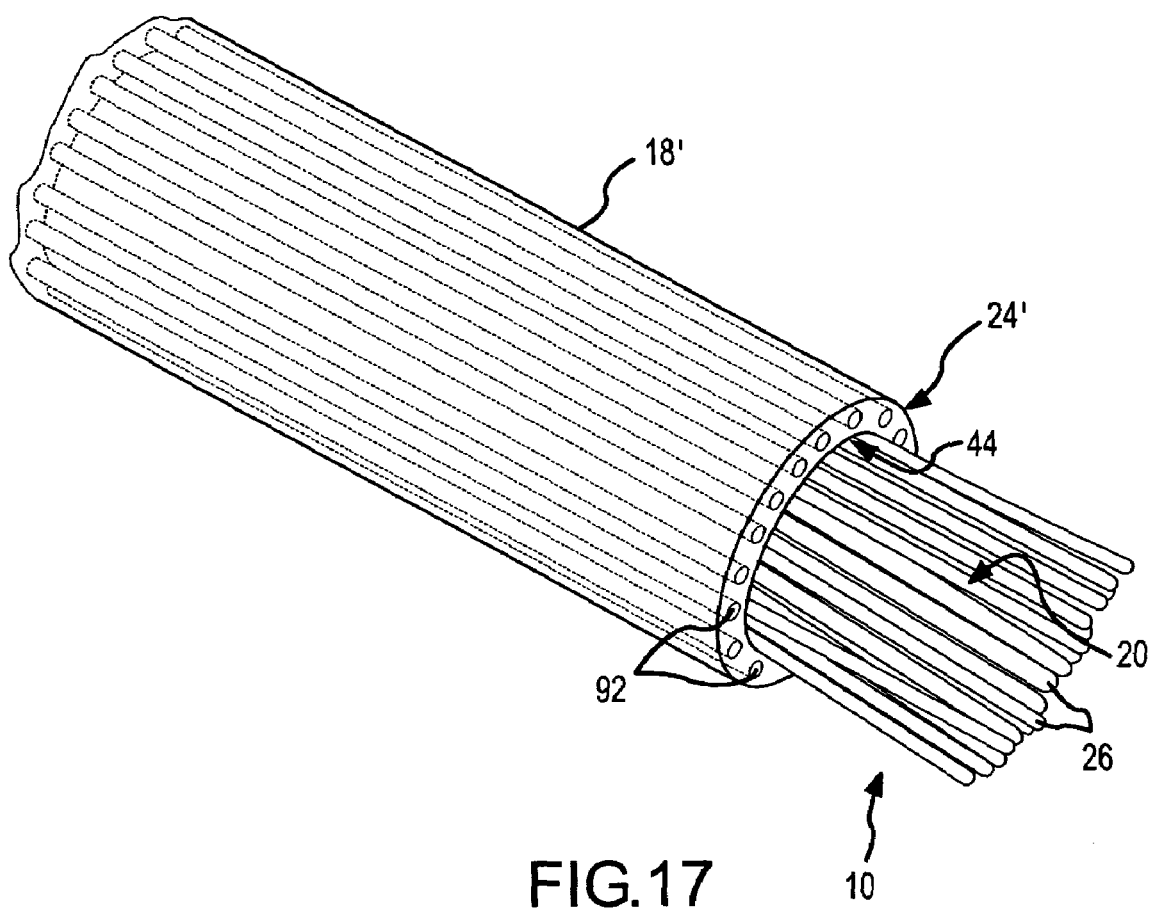
FIG. 17 is a fragmentary, isometric view of an embodiment of the shaft of the surgical pencil having a concentric ring of sub-channels around a main or central channel through which the filaments extend.

FIG. 17 depicts an embodiment of the pencil shaft 18' having a concentric ring of tubes 92 within the wall of the pencil shaft 18' that defines the central lumen 44 through which the brush filaments 26 extend. The circumferential ring of tubes 92 around the lumen 44 may be used to carry conductive or nonconductive fluid, including therapeutic fluid or medicine. The embedded tubes 92 depicted in this figure could define spiral or helical paths toward the distal end 24' of the pencil shaft 18', similar to the paths or channels 104 described below in connection with FIGS. 19 and 20.

Figure 18:
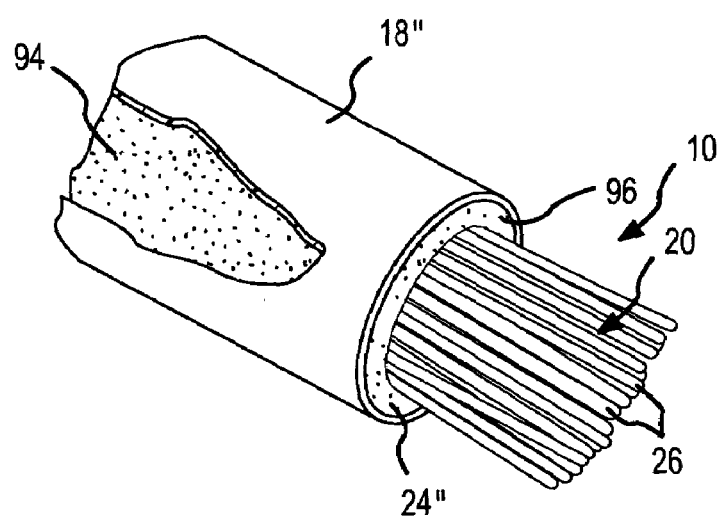
FIG. 18 is a fragmentary, isometric view of an embodiment wherein a porous inner sheath surrounds the filaments of the brush electrode adjacent to the exposed portion of the brush electrode.

FIG. 18 depicts an embodiment wherein a porous sheath 94 surrounds the filaments 26 of the brush electrode 10 adjacent to the exposed portion 20 of the brush electrode 10. An outer covering 18'', possibly a thin, unitary extension of the pencil shaft, may be placed around the outer cylindrical surface of the porous sheath 94. An angular ring of material 96 may be exposed at the distal end 24'' of the porous sheath 94 adjacent to the exposed portion 20 of the brush electrode 10.

Figure 19:
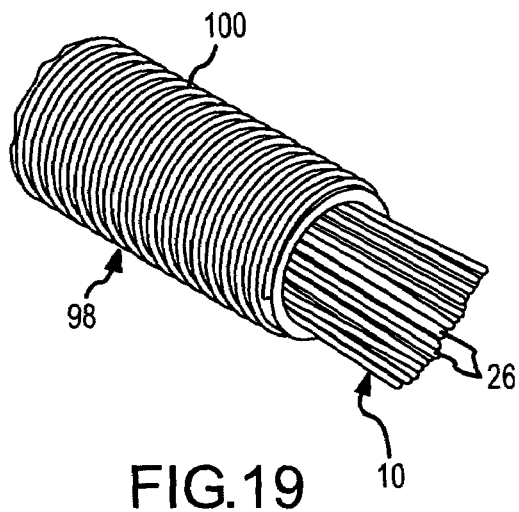
FIG. 19 is a fragmentary, isometric view of an embodiment wherein a threaded inner sheath, having a spiral or helical ridge on its outer surface, surrounds the filaments of the brush electrode adjacent to the exposed portion of the brush electrode.
Figure 20:
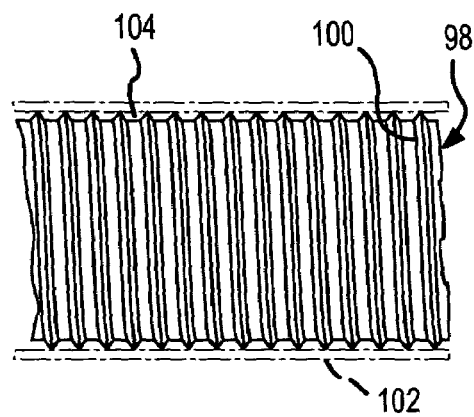
FIG. 20 is a fragmentary view of a section of the threaded inner sheath depicted in FIG. 19, surrounded by the pencil shaft shown in phantom and cross-section to create a helical flow channel between the threaded inner sheath and the surgical pencil shaft.

FIG. 19 is a fragmentary, isometric view of an embodiment wherein a threaded sheath 98 surrounds the filaments 26 of the brush electrode 10. The threaded sheath 98 has a spiral or helical ridge 100 on its outer surface. As shown to good advantage in FIG. 20, when the threaded sheath 98 is inserted into an outer covering 102, possibly a thin, unitary extension of the pencil shaft (shown in phantom and cross-section), a helical flow channel 104 is created between the threaded sheath 98 and the outer covering 102. Conductive fluid, nonconductive fluid, or medication may be delivered to the tissue adjacent to the brush electrode 10 via this flow channel 104.

Figures 21, 22:
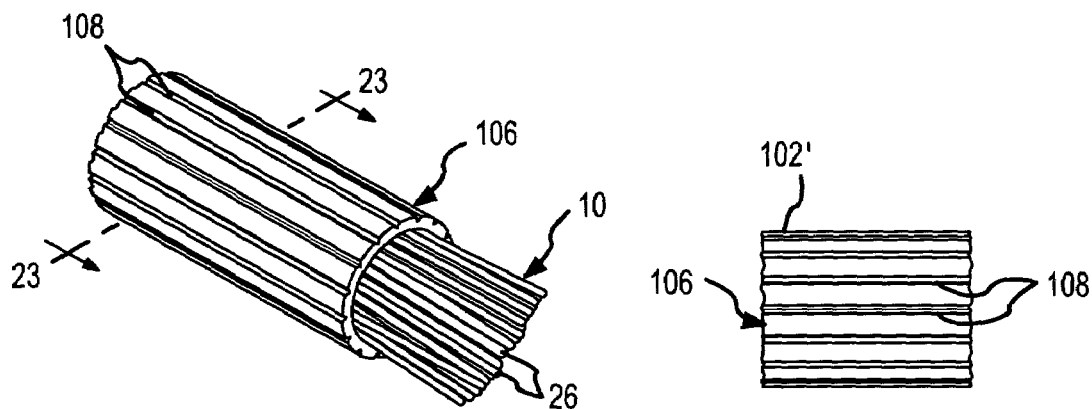
FIG. 21 is a fragmentary, isometric view of an embodiment wherein a grooved sheath, having a plurality of longitudinally-extending grooves or cuts on its outer surface, surrounds the filaments of the brush electrode adjacent to the exposed portion of the brush electrode.
FIG. 22 is a fragmentary view of a section of the grooved sheath depicted in FIG. 21, surrounded by the pencil shaft (shown cross-section) to create a plurality of longitudinally-extending flow channels between the grooved sheath and the surgical pencil shaft.
Figure 23:
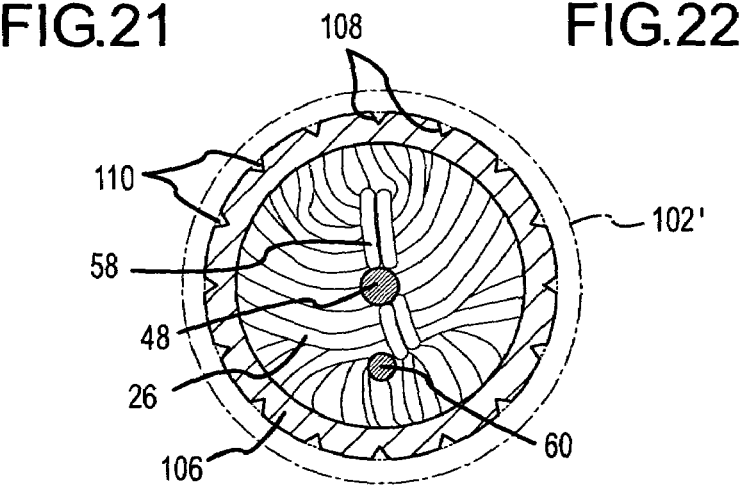
FIG. 23 is a cross-sectional view taken along line 23-23 of FIG. 21, with the surgical pencil shaft shown in phantom and with the longitudinally-extending flow channels clearly visible.

FIG. 21 is a fragmentary, isometric view of another embodiment, wherein a grooved sheath 106 surrounds the filaments 26 of the brush electrode is. The grooved sheath 106 has a plurality of longitudinally-extending grooves or cuts 108 formed on its outer surface, adjacent to the exposed portion of the brush electrode 10. FIG. 22 is a fragmentary view of a section of the grooved sheath 106 depicted in FIG. 21, surrounded by an outer covering 102', possibly a thin, unitary extension of the pencil shaft (shown in cross-section) to create a plurality of longitudinally-extending flow channels 110 (shown to better advantage in FIG. 23) between the grooved sheath 106 and the covering 102'. As shown in FIG. 23, when the grooved sheath 106 is inserted into the outer covering 102' (shown in phantom and cross-section), the plurality of longitudinally-extending flow channels 110 are created between the grooved sheath 106 and the outer covering 102'. Again, conductive fluid, nonconductive fluid, or medication may be delivered to the tissue 46 adjacent to the brush electrode 10 via these flow channels 110.

Figure 24:
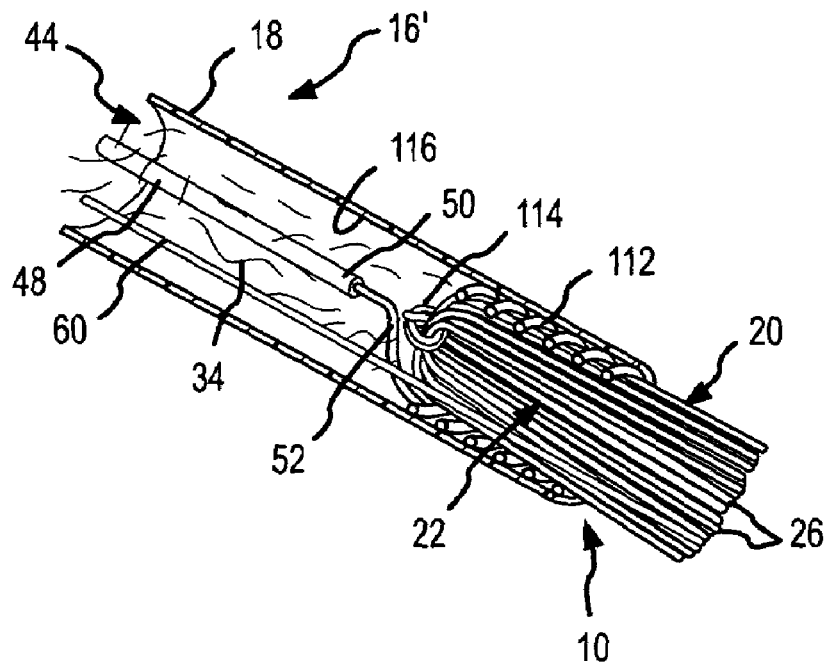
FIG. 24 is similar to FIG. 5, but depicts an isometric, cross-sectional view of the shaft of a surgical pencil, wherein the primary conductor makes electrical contact with the filaments via an energy transfer coil or spring surrounding at least the embedded portion of the brush electrode.
Figure 25:
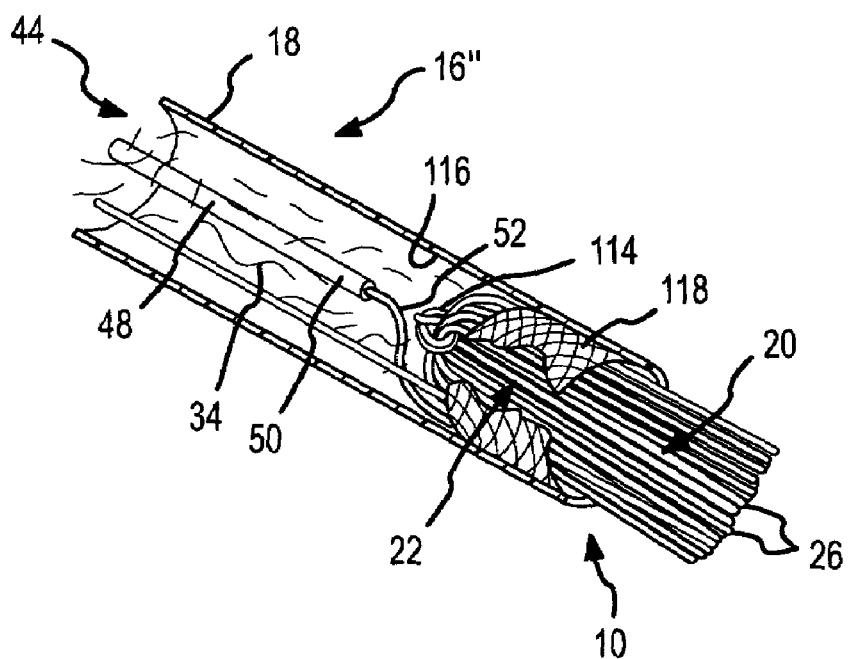
FIG. 25 is similar to FIGS. 5 and 24, but depicts an isometric, cross-sectional view of the shaft of a surgical pencil, wherein the primary conductor makes electrical contact with the filaments via an energy transfer mesh or fabric surrounding at least the embedded portion of the brush electrode.

FIGS. 24 and 25 depict alternative mechanical interfaces between the filaments 26 of the brush electrode 10 and the primary conductor 48. FIG. 24 is similar to FIG. 5, but depicts an isometric, cross-sectional view of a surgical pencil 16' wherein the exposed portion 52 of the primary conductor 48 makes electrical contact with the brush filaments 26 via an energy transfer coil or spring 112 surrounding at least the embedded portion 22 of the brush electrode 10. In this embodiment, the RF energy is transferred to the brush electrode 10 over a large surface area (i.e., over the entire inner surface area of the coil 112). Thus, less damage to the filaments 26 may occur in this embodiment than may occur in the embodiment depicted in FIG. 5, wherein all of the RF energy is transferred from the uninsulated portion 52 of the primary conductor 48 to the brush electrode 10 at the single connection point 56. As depicted in FIG. 24, a loop of wire 114 may be present to help collect and stabilize the filaments 26 during assembly of the surgical pencil 16'. This loop of wire 114 may be anchored to, for example, the inner surface 116 of the pencil shaft 18. As previously described, a secondary lead 60 may also be present in the lumen 44 of the pencil shaft 18.

FIG. 25 is similar to FIGS. 5 and 24, but depicts an isometric, cross-sectional view of a surgical pencil 16'' wherein the primary conductor 48 makes electrical contact with the filaments 26 of the brush electrode 10 via an energy transfer mesh or fabric 118 surrounding at least the embedded portion 22 of the brush electrode 10. This embodiment has the same advantages that were just described for the embodiment depicted in FIG. 24.

Figure 26:
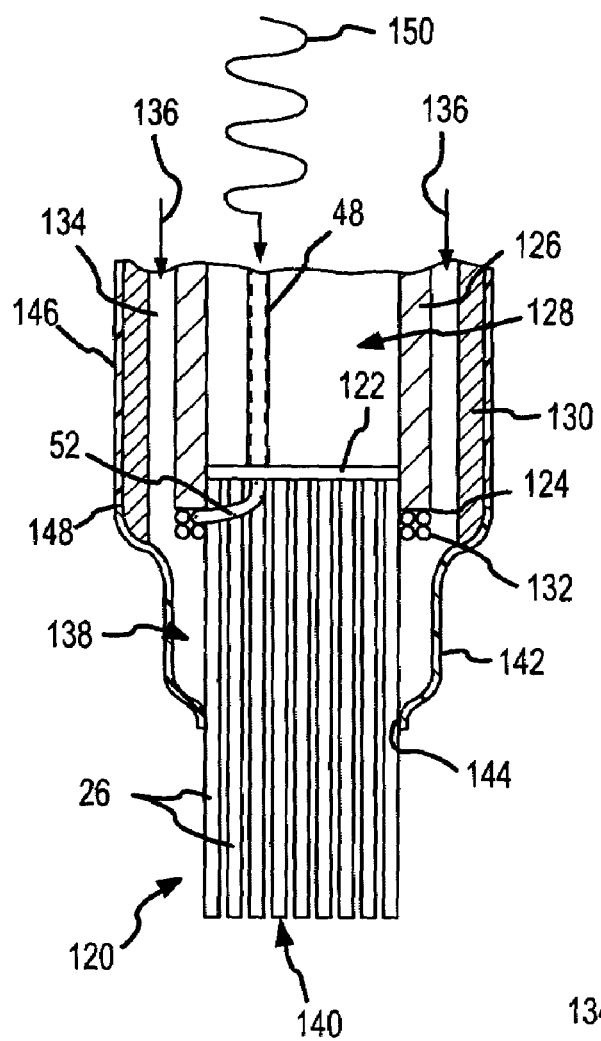
FIG. 26 is a cross-sectional view of a first embodiment of a shielded-tip brush electrode, wherein an uninsulated portion of the primary conductor is looped around the outer surface of the brush electrode.

FIG. 26 is a cross-sectional view of a first embodiment of a shielded-tip brush electrode 120. In this embodiment, the uninsulated portion 52 of the primary conductor 48 is looped around the outer surface of the brush electrode after passing through a mechanical interface 122 supporting the filaments 26 of the shielded-tip brush electrode 120 adjacent to the distal end 124 of an inner sheath 126. Since fluid may or may not travel through the lumen 128 of the inner sheath 126, the mechanical interface 122 may or may not be porous. It should be noted that, although the filaments 26 are shown as extending only into the distal end 124 of the inner sheath 126, the filaments 26 may extend further into the inner sheath 126 and may even extend all the way to the proximal end (not shown) of the surgical pencil.

In the embodiment depicted in FIG. 26, the pencil shaft 130 surrounds the inner sheath 126. The inner sheath 126 houses the primary conductor 48 and supports the mechanical interface 122 for the filaments 26 of the brush electrode 120. The primary conductor 48 again includes an uninsulated portion 52 that transfers RF energy 150 to the conductive filaments 26 in the shielded-tip brush electrode 120. As mentioned, in this embodiment the uninsulated portion 52 of the primary conductor 48 forms loops or coils 132 around the circumference of the brush electrode 120. These loops or coils 132 increase the surface area through which the RF energy 150 is transferred, thereby providing more effective, and potentially less destructive, energy transfer to the brush electrode 120.

As shown in FIG. 26, the pencil shaft 130 is placed around the inner sheath 126, but is radially and longitudinally offset from the inner sheath 126. The radial offset creates an annular gap or channel 134 between the inner sheath 126 and the pencil shaft 130 through which conductive fluid 34 may, for example, be introduced to the sides of the filaments 26. The conductive fluid 34, if present, would flow through the annular channel 134 in the direction of the arrows 136 shown at the top of FIG. 26. The longitudinal offset between the inner sheath 126 and the pencil shaft 130 ensures that the channel 134 for the conductive fluid 34 extends past the distal end 124 of the inner sheath 126 to the sides of the filaments 26. In this embodiment, the conductive fluid 34 would flow through the annular channel 134 between the inner sheath 126 and the pencil shaft 130, past the coils 132 of uninsulated conductive wire, into an annular fluid jacket 138 surrounding a region of the brush electrode 120 adjacent to the distal ends of the inner sheath 126 and pencil shaft 130, and then into the sides of the brush electrode 120 itself and through the interstitial gaps between the filaments 26 comprising the brush electrode 120. The RF energy 150 is thus carried by the conductive fluid 34 into the core of the brush electrode 120 and toward its working surface 140.

In this embodiment, a flexible polymer nipple or boot 142, defining an outer wall of the annular fluid jacket 138, also supports the filaments 26 in a ring 144 of direct contact extending around the perimeter of the bundle of filament 26. The flexible boot or nipple 142 may be porous. In the circumstance that the brush electrode 120 is provided on the distal end of an endoscopic or laparoscopic device, a smooth outer wall 146 to facilitate easier insertion and manipulation of the endoscopic or laparoscopic surgical device in a patient may cover the pencil shaft 130 and abut a corresponding edge 148 of the flexible polymer nipple or boot 142. Alternatively, the material of the outer wall 146 may actually form the nipple or boot 142 in addition to forming covering around the perimeter of the pencil shaft 130 (or endoscope or laparoscope cannula). An annular layer of porous material or mesh fabric (not shown) may be placed in the annular fluid jacket 138 to keep the filaments 26 wetted and to help prevent splaying (see FIGS. 41-43) of the brush electrode 120.

Figure 27:
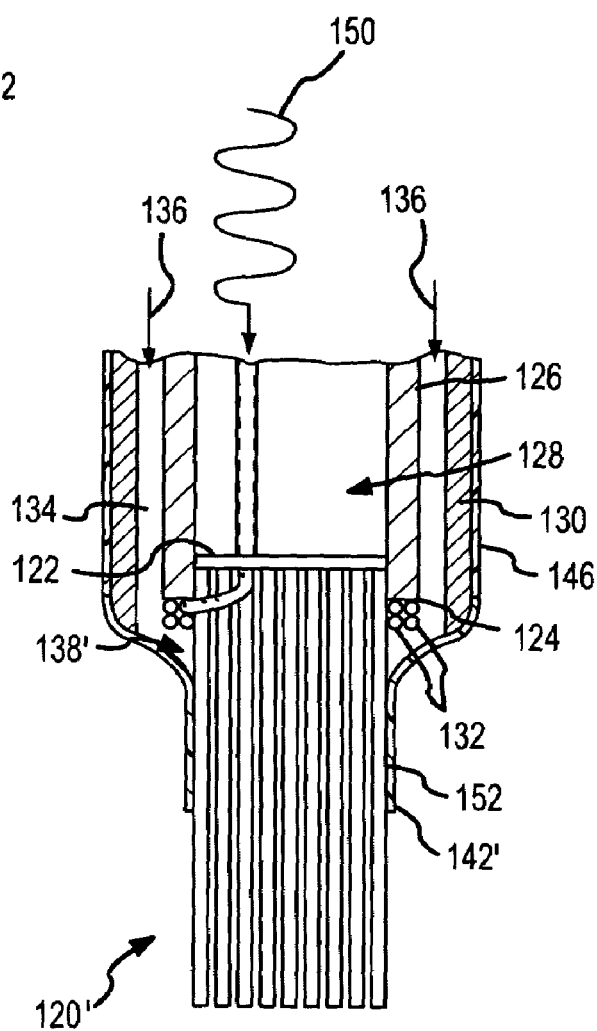
FIG. 27 is similar to FIG. 26, but depicts a second embodiment of a shielded-tip brush electrode.

FIG. 27 is similar to FIG. 26, but depicts a second embodiment of a shielded tip brush electrode 120'. The only differences between the embodiment depicted in FIG. 26 and the embodiment depicted in FIG. 27 are the size of the fluid jacket and the configuration of the flexible polymer nipple or boot that supports the brush filaments. In the embodiment depicted in FIG. 27, an alternative flexible polymer nipple or boot 142' defines a smaller fluid jacket 138' and supports the filaments 26 in a band of direct contact 152 extending around the perimeter of the bundle of filaments 26. The band of direct contact 152 supports the filaments 26 over a larger section of the outer surface of the brush electrode 120' than does the ring of direct contact 144 depicted in FIG. 26. By adjusting the configuration of the flexible polymer nipple or boot 142' in this manner, the amount of conductive fluid flowing into the brush electrode and the overall flexibility of the brush electrode can be manipulated.

FIGS. 28-35 depict different cross-sectional configurations for brush electrodes 10 according to the present invention. Interstitial spaces 156 are clearly visible in each of these figures. In FIGS. 28-31, the brush electrode 10 has a conductive core 154. In these four figures, the conductive filaments 72 are shown with cross hatching, and the nonconductive filaments 74 are shown without cross hatching. Thus, the brush electrode 10 depicted in FIG. 28 is fully conductive and does not have any nonconductive filaments 74. In each of the embodiments depicted in FIGS. 29-31, a conductive core 154 is shielded by a barrier of nonconductive filaments 74. In particular, FIG. 29 depicts a core of relatively large conductive filaments 72 surrounded by two rings of nonconductive filaments 74 of approximately the same size. In FIG. 30, a core 154 of relatively small conductive filaments 72 is surrounded by two rings of relatively large nonconductive filaments 74. In FIG. 31, a conductive core 154 of relatively large conductive filaments 72 is surrounded by two rings of relatively small nonconductive filaments 74.

Figure 32:
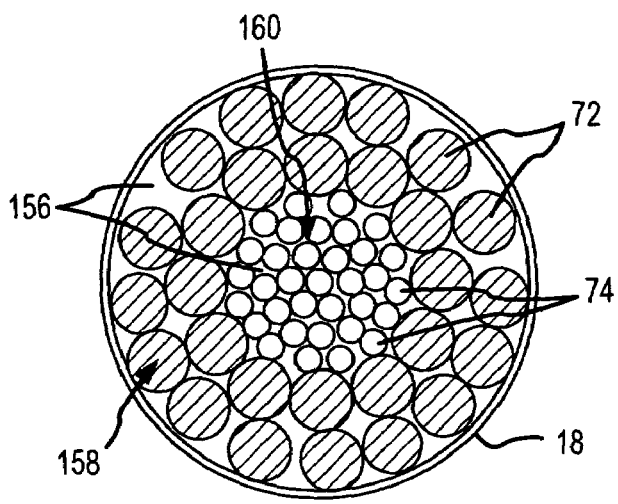
Figure 33:
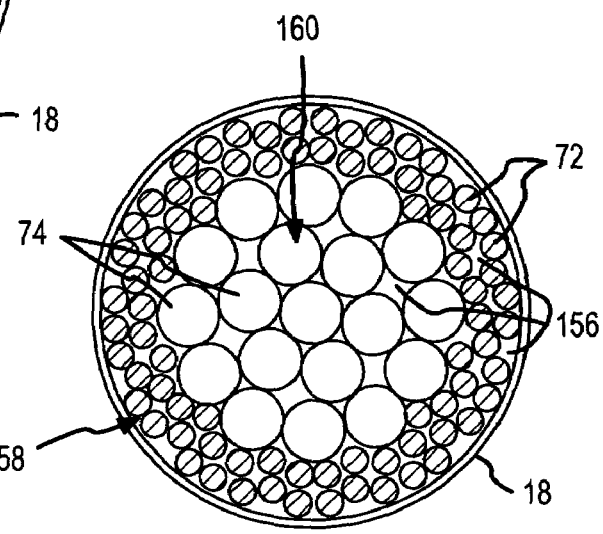

FIGS. 32 and 33 depict cross-sectional configurations for brush electrodes 10 that have conductive perimeters 158. Thus, in the embodiments depicted in FIGS. 32 and 33, a nonconductive core 160 of nonconductive filaments 74 is surrounded by conductive filaments 72. FIG. 32 depicts a core of relatively small nonconductive filaments 74 surrounded by two rings of relatively large conductive filaments 72. In FIG. 33, a core 160 of relatively large nonconductive filaments 74 is surrounded by two rings of relatively small conductive filaments 74.

Figure 34:
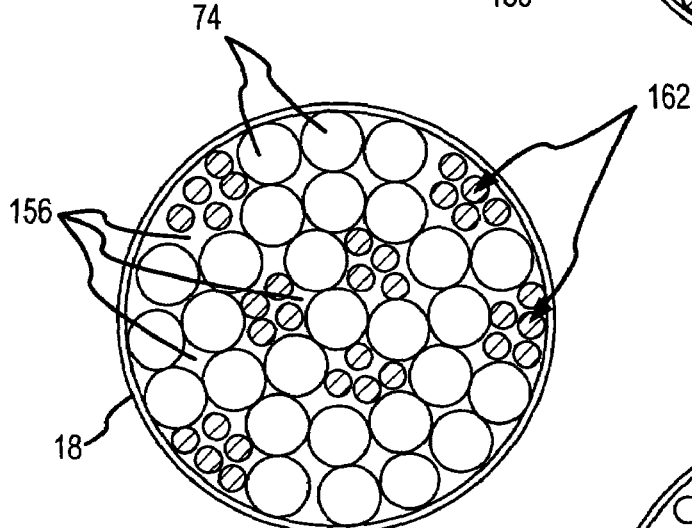
Figure 35:
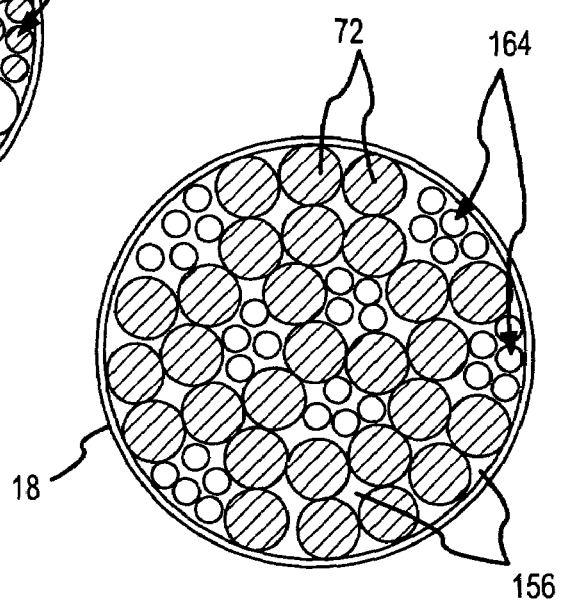

In FIG. 34, conductive clusters 162 of relatively small filaments are interspersed among relatively large nonconductive filaments 74. The interspersed conductive clusters 162 may be interspersed in a specific pattern, pseudo randomly, or randomly among the nonconductive filaments 74 in order to achieve a desired electric field from the resulting brush electrode 10. In FIG. 35, nonconductive clusters 164 of relatively small filaments are interspersed among relatively large conductive filaments 72.

Figure 36:
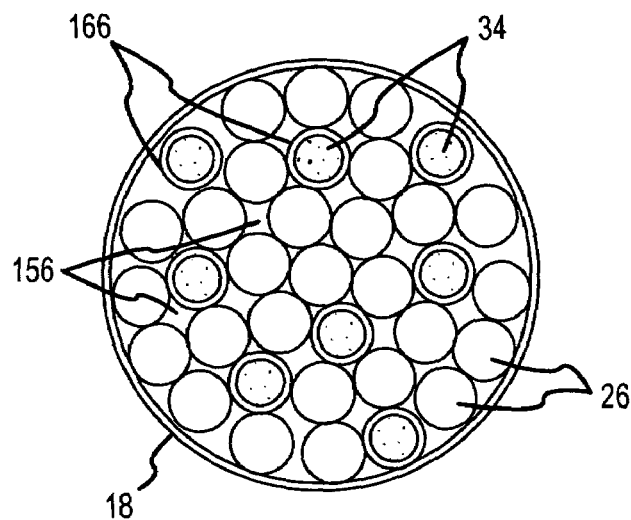
FIG. 36 is a cross-sectional view of a brush electrode wherein some of the filaments comprise hollow or porous members.

FIG. 36 is a cross-sectional view of a brush electrode 10 wherein some of the filaments are hollow or porous 166. Such hollow or porous filaments 166 may be used as conduits for conductive fluid 34, they may be used to supply therapeutic medications, and they may provide suction ports at the brush-tissue interface to control field smearing on the tissue surface. If the filaments are porous, they may retain a small amount of fluid in pores that are oriented at various angles to the longitudinal axis of the filaments. During a surgical procedure, some of the RF energy 150 may dehydrate the porous filaments 166 before affecting the surrounding blood, particularly when the conductivity of the tissue 46 lessens as the surgical procedure progresses. Thus, if excess RF energy 150 is present during a procedure, that energy may harmlessly dehydrate the porous filaments 166 rather than negatively affecting the tissue 46 being treated by the brush electrode 10 or the blood in the area of that tissue 46. In the embodiment depicted in FIG. 36, the other filaments 26 may be conductive or nonconductive filaments.

Figure 37:
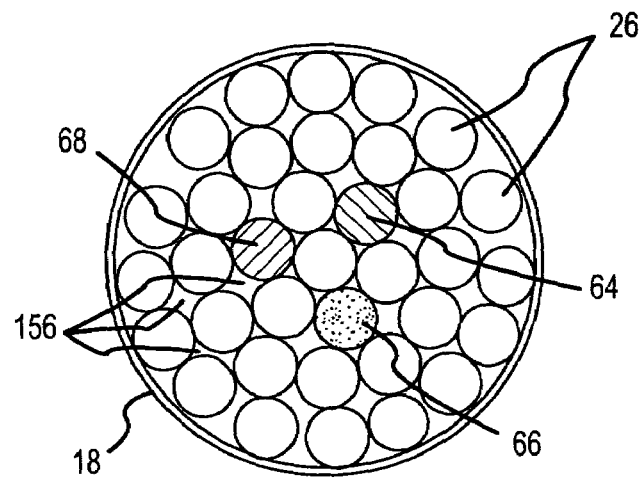
FIG. 37 is a cross-sectional view of a brush electrode having devices (e.g., a thermocouple or other temperature sensor, a pressure sensor, or an ultrasound sensor) embedded among the filaments.

FIG. 37 is a cross sectional view of a brush electrode 10 having devices 64, 66, 68 embedded among the conductive and nonconductive filaments 26. The devices may include, for example, pressure sensors 68 to measure contact pressure between the brush electrode 10 and the tissue, thermal sensors 64 (e.g., a thermocouple) at the tip of the brush electrode 10 to sense the brush-tissue interface temperature, or fiber optic or ultrasound sensors 66 for in situ lesion identification and characterization. The devices may be operatively connected to equipment (not shown) at the proximal end of the surgical pencil 16 by secondary leads like the secondary lead 60 depicted in, for example, FIGS. 5 and 8-16.

Figure 38:
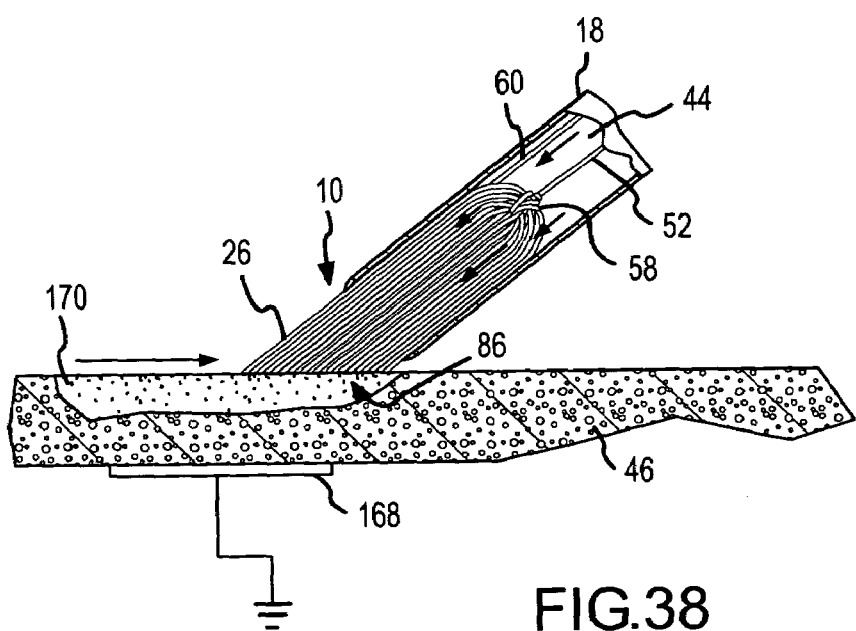
FIG. 38 is a cross-section view of the distal tip of a surgical device having a brush electrode with an angled tip according to the present invention forming linear or drag lesion on a section of tissue.

FIG. 38 is a fragmentary, partial cut-away view of a surgical pencil 16 having a brush electrode 10 with a wedge-shaped tip 86 according to FIG. 14 of the present invention forming a lesion 170 on a section of tissue 46. As shown in this figure, the brush electrode 10 is placed against the tissue 46 with its filaments 26 in contact with or in close proximity to the tissue 46. The conductive filaments are connected to, for example, an RF source in the base unit 14 and serve as the active electrode. A ground plate 168 is affixed to another part of the patient's body with a large surface area, for example, the thigh, and acts as the passive electrode to ground. When present, conductive fluid 34 from a fluid source (e.g., the base unit 14) flows through the lumen 44 (e.g., FIG. 5) of the surgical pencil 16 and through the brush filaments 26 to the working surface at the brush tip, thereby creating a wet-brush electrode. The brush electrode 10 can be localized on the tissue 46 to create a spot or point lesion, or the brush electrode 10 may be dragged along the surface of the tissue 46 to create a continuous linear lesion 170, as shown in FIG. 38.

Figure 39:
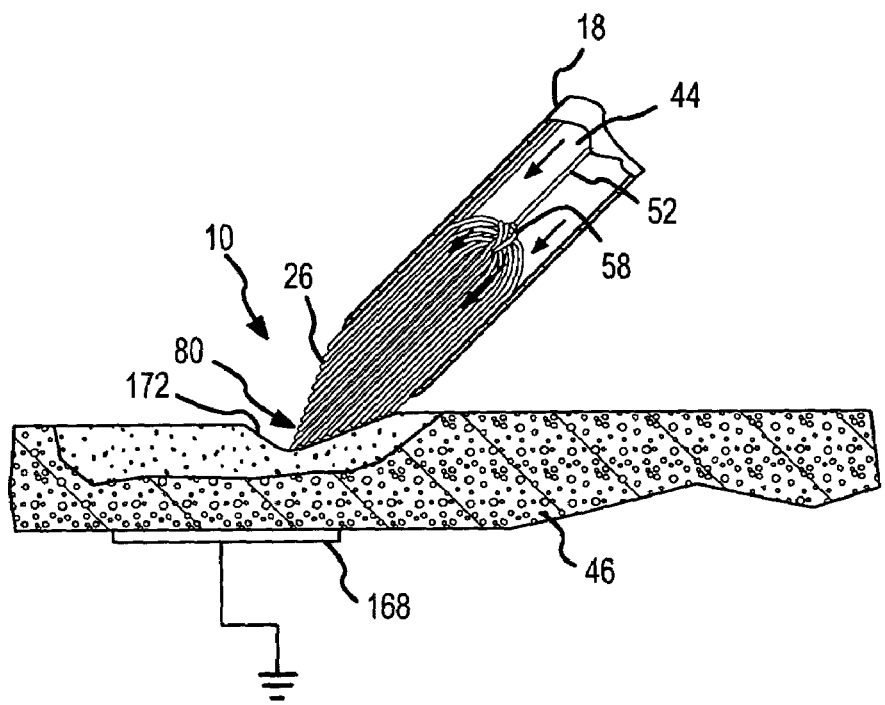
FIG. 39 is a cross-section view of the distal tip of a surgical device having a brush electrode with a pointed tip forming a deep lesion on a section of tissue.

FIG. 39 is a fragmentary, partial cut-away view of a surgical pencil 16 having a brush electrode 10 with a triangular tip 80 according to FIG. 11 of the present invention forming a lesion 172 on a section of tissue 46. The embodiment of FIG. 39 is similar to that of FIG. 38 except for the resulting lesion created. In FIG. 39, a deep lesion 172 is formed as opposed to the surface lesion 170 of FIG. 38. The triangular tip 80 may be operated similar to a blade. If higher power electrosurgical energy were applied, the brush electrode 10 with the triangular tip 80 may function similar to an electrosurgical scalpel and create an incision in the tissue 46.

Figure 40:
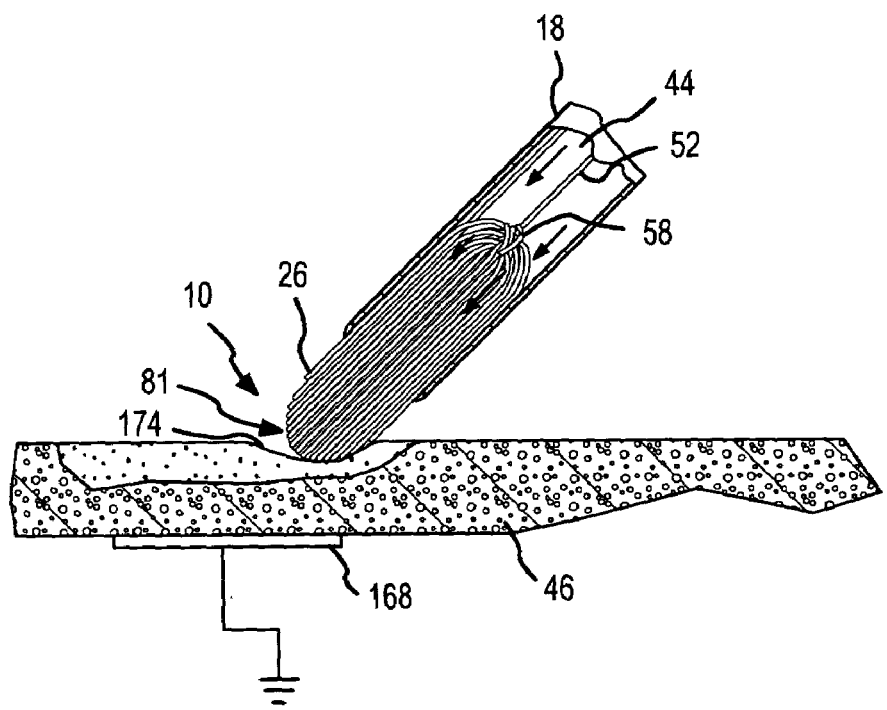
FIG. 40 is a cross-section view of the distal tip of a surgical device having a brush electrode with a rounded tip forming a shallow lesion on a section of tissue.

FIG. 40 is a fragmentary, partial cut-away view of a surgical pencil 16 having a brush electrode 10 with a convex tip 84 according to FIG. 13 of the present invention forming a lesion 174 on a section of tissue 46. The embodiment of FIG. 40 is similar to that of FIG. 38 except for the resulting lesion created. In FIG. 40, a shallow lesion 172 is formed as opposed to the surface lesion 170 of FIG. 38 or the deep lesion 172 of FIG. 39. The convex tip 84 provides more concentrated energy toward the center of the brush electrode 10. If higher power electrosurgical energy were applied, the brush electrode 10 with the convex tip 80 may function similar to a cauterizing or coagulation device to arrest bleeding, or alternately may be used to remove undesirable surface tissue 46, for example, a mole or tumor. Further, the convex tip makes better contact with uneven, undulating, or trabecular tissue surfaces to aid in the creation of uniform, linear lesions on such surfaces.

Figure 41:
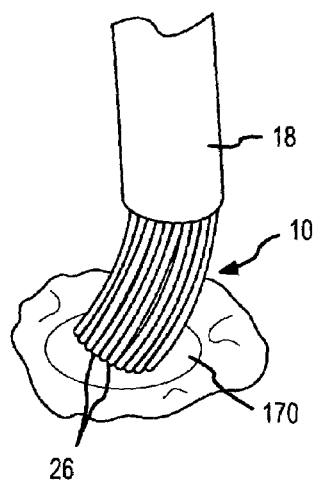
FIGS. 41-43 depict a brush electrode according to the present invention forming different-sized lesions based in part upon the amount of splay of the brush electrode.
Figure 42:
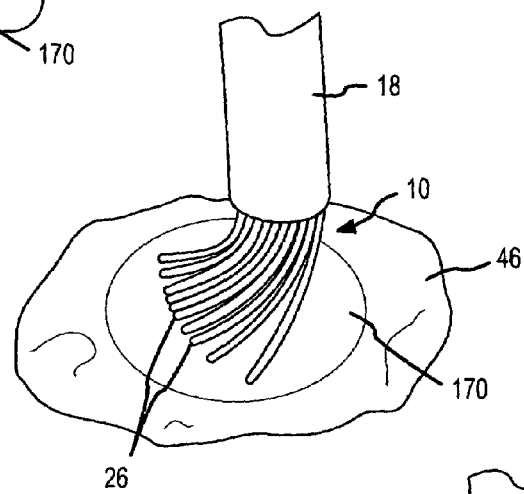
Figure 43:
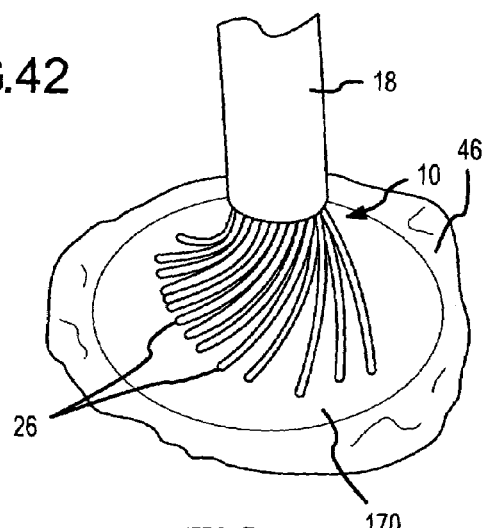

FIGS. 41-43 depict a brush electrode 10 according to the present invention forming different size spot lesions 12 based in part upon the amount of splay of the brush electrode 10. In FIG. 41, relatively light contact pressure is being used to press the brush electrode 10 against the tissue 46 while forming a lesion 12. This application of light pressure results in minimal splaying of the filaments 26 comprising the brush electrode 10, and thus a relatively small lesion 12 is formed. In FIG. 42, more pressure is being used to press the brush electrode 10 into contact with the tissue 46, resulting in relatively more splaying of the brush electrode 10. As long as the efficiency of the brush electrode 10 is not degraded too greatly by the splaying, a relatively larger lesion 12 may thus be formed by applying additional pressure to press the brush electrode 10 toward the tissue 46. In FIG. 43, even more contact pressure is being applied to the brush electrode 10 than is being applied in FIGS. 41 and 42, resulting in even more splaying of the brush electrode 10 and the formation of a relatively larger lesion 12 on the tissue 46 than is being formed in FIGS. 41 and 42.

Figure 44:
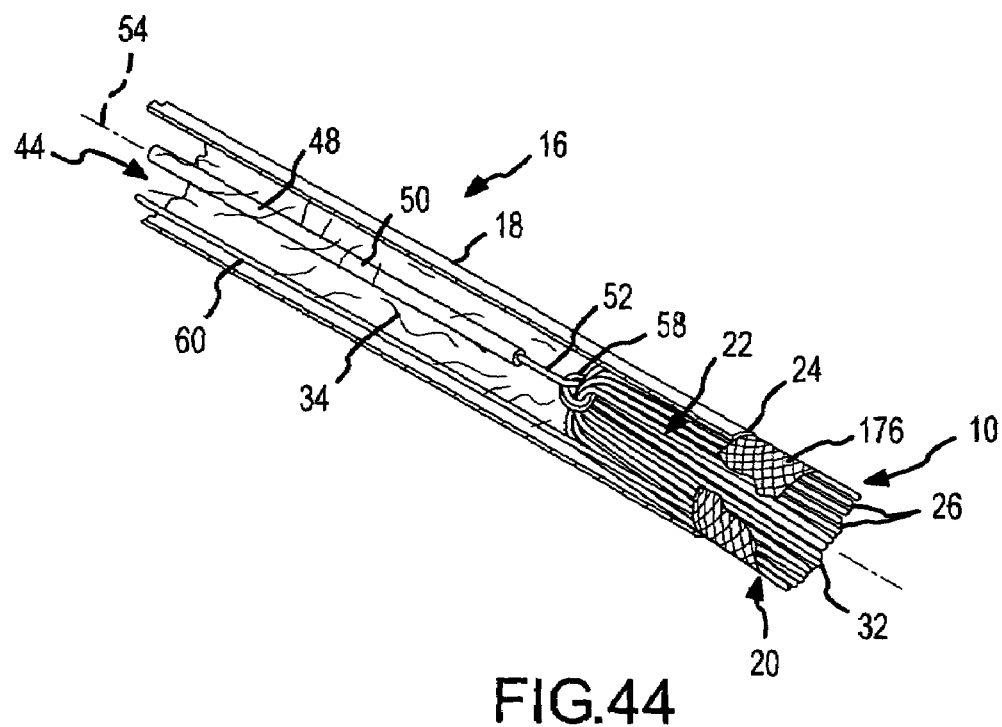
FIG. 44 is a cross-section view of the distal tip of a surgical device having a brush electrode surrounded by a mesh fabric.
Figure 45:
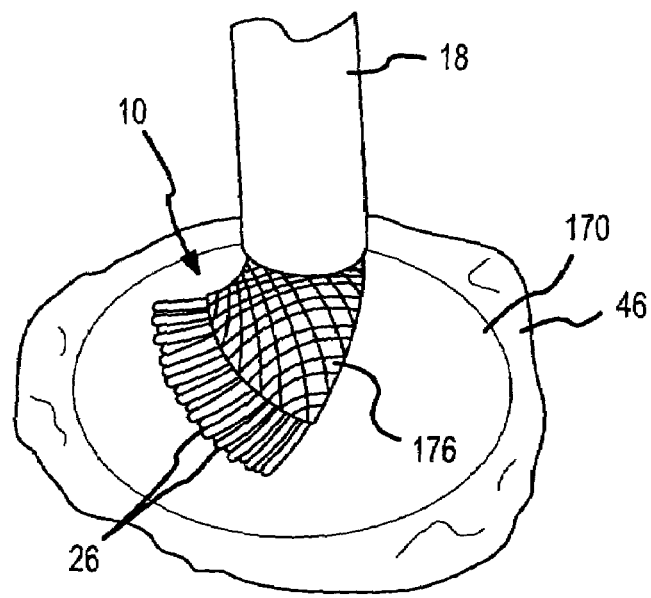
FIG. 45 is an isometric view of the brush electrode of FIG. 44 depicting the mesh fabric reducing the splaying of the filaments.

FIGS. 44 and 45 depict an alternative embodiment of a surgical pencil 16 with a brush electrode 10, which includes a fabric or mesh jacket 176 about a proximal section of the exposed portion 20 of the filaments 26. The fabric or mesh jacket 176 acts to reduce the slaying of the filaments 26 if the application so requires. The fabric or mesh jacket 176 may be made of a conductive or nonconductive material depending upon the desired electric field effects for the brush electrode 10. The fabric or mesh jacket 176 may similarly be absorptive if it is desirable to retain fluid about the filaments 26 for cooling or other purposes. The proximal end of the fabric or mesh jacket 176 may be affixed to the distal end of the pencil shaft 18 or it may extend into the lumen 44 of the pencil shaft 18 and cover a section of the embedded portion 22 of the filaments 26. The fabric or mesh jacket 176 may also extend distally to the distal tip 32 of the brush electrode 10 completely restrict any splay in the filaments 26.

Figure 46:
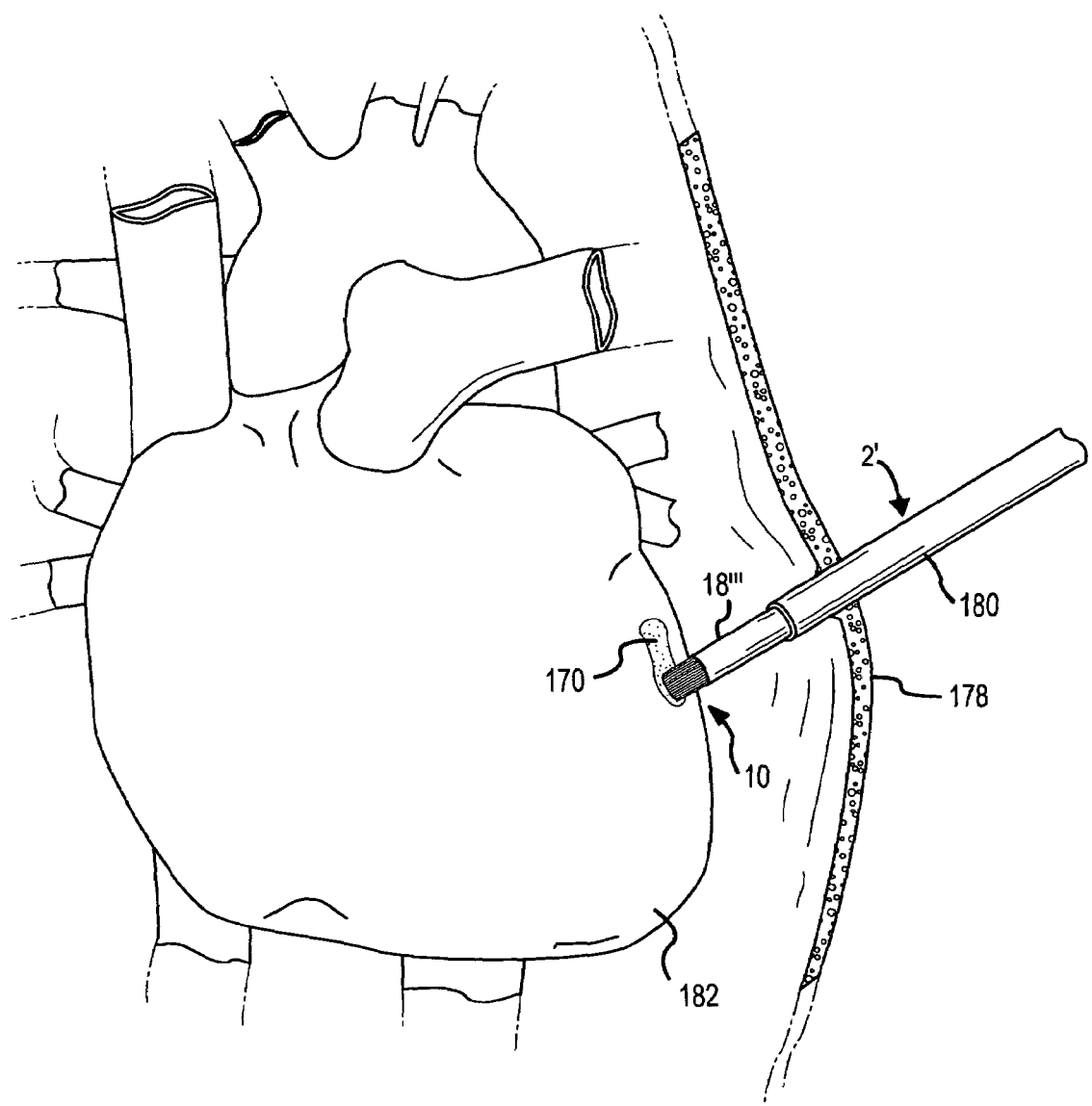
FIG. 46 is a schematic view of an alternate embodiment of the invention wherein the surgical device is a thoracoscopic instrument with a brush electrode forming a lesion on a heart.

FIG. 46 depicts an alternate embodiment of the invention wherein the surgical device is a thoracoscopic instrument 2', rather than a surgical pencil, for use with a thoracope. Minimally invasive scope surgery options, when available, generally reduce the trauma to a patient compared to open cavity surgery and result in faster and improved patient recovery. The exemplary thoracoscopic instrument 2' is composed of an introducing cannula 180 with a lumen. Inserted within the lumen is a thoracoscopic shaft 18''' with a brush electrode 10 according to the present invention positioned on a distal end of the thoracoscopic shaft 18'''. As depicted in FIG. 46 the thoracoscopic instrument 2' may be inserted into a patient's body via a small incision in the skin 178, muscle, and other tissue. The introducing cannula 180 is inserted into the incision and directed into the body cavity adjacent the location of the surgical procedure to be performed. The thoracoscopic shaft 18''' is inserted within the lumen of the introducing cannula 180 and translated distally to position the brush electrode 10 in contact with the tissue to be treated. In the schematic of FIG. 46 the brush electrode 10 on the thoracoscopic instrument 2' is shown within the pericardium creating a lesion 170 on the epicardium of the heart 182, for example in a maze-like procedure. In addition to thoracoscopic instruments, surgical devices according to the present invention may also take the form of endoscopic instruments, laparoscopic instruments, arthroscopic instruments, or any other scope surgical device.

The surgical device with a brush electrode according to the present invention delivers therapeutic RF energy to the tissue via the conductive filaments alone, via the conductive fluid alone, or via both the conductive filaments and the conductive fluid. In the latter two configurations, the brush electrode is referred to as a wet-brush electrode. Since it is possible for the conductive fluid to escape from the exposed portion of the wet-brush electrode before reaching the working surface at the distal tip of the wet-brush electrode, there is some RF energy leakage to the surrounding blood or tissue. The leakage of therapeutic energy to the surrounding blood or tissue is in part due to direct contact between the blood or tissue and the conductive filaments and in part due to the conductive fluid escaping between the filaments to the surrounding blood or tissue, particularly when substantial splaying of the filaments occurs (see, e.g., FIG. 43). Further, when using the surgical device in a blood-filled environment, the blood will further dilute the electric field created and act as a coolant, resulting in shallower lesions than would be created on dry tissue surfaces.

Different effects (e.g., incision, ablation, coagulation, cauterization, fulguration, and desiccation) may be achieved with the surgical device depending upon the presence or absence of fluid, the power of the therapeutic RF energy transmitted to the brush electrode, the waveform of the therapeutic energy, and the shape of the working surface of the electrode. For example, higher power RF energy is typically used for electrosurgical procedures such as creating incisions and cauterization. In addition, a sharply pointed working surface of the brush electrode may facilitate the creation of incisions, while a flatter working surface coupled with high energy may be preferable for large area cauterization. Alternately, lower power and a flatter working surface may be preferred for ablation or coagulation effects (e.g., for the treatment of varicose veins). However, a sharper working surface may be preferred for removal of tissue, for example, a tumor.

The design parameters for the brush electrode of the surgical device include both filament and brush parameters. The filament parameters include, for example, the material and structural properties of the individual filaments (e.g., what material(s) each individual filament is constructed from, whether the filaments are hollow or solid, whether the filaments are porous, and how flexible or stiff the filaments are), the shape and cross-sectional areas of the individual filaments, and the electrical conductivity of the individual filaments. The electrical conductivity of the individual filaments may be constant along the length of the filaments or may vary along the length of the filaments. Also, if the conductivity of a filament varies along its length, it may vary continuously or discontinuously. The filament design parameters may be different for each filament.

The design parameters for the brush electrode of the surgical device include, for example, the overall shape and cross-sectional area of the brush (i.e., the overall shape and size of the filament bundle forming the brush electrode), the tip length of the brush itself (i.e., the length of the portions of the filaments that extend the farthest from the distal end of the pencil shaft), the shape of the brush tip, the length of the individual filaments relative to each other, the packing density of the filaments comprising the brush, and the overall electrical resistance of the brush. When both nonconductive and conductive filaments are present, the conductive filaments may be distributed evenly, randomly, or pseudo-randomly among the nonconductive filaments comprising the brush electrode.

By controlling, among other things, the cross-sectional shapes of the filaments, the cross-sectional areas of the filaments, the flexibility or stiffness of the filaments, the packing density of the filaments, the ratio of the nonconductive filaments to the conductive filaments, and the placement of the nonconductive and conductive filaments relative to each other, it is possible to obtain brush electrodes having desired electrical and thermal characteristics, which ultimately determine the types of lesions that may be created when using the brush electrodes for surgical treatment. As mentioned above, it is even possible to vary the mechanical and electrical properties of each individual filament, if necessary, to achieve desired results.

The shapes and cross-sectional areas of the individual filaments and the packing density of the brush electrode affect the interstitial spaces between the filaments. The interstitial spaces between the filaments determine the flow path of the conductive or nonconductive fluid when the brush electrode is being used as a wet-brush electrode. The flow path of the conductive or nonconductive fluid determines to a great extent the electrical and thermal characteristics of the wet-brush electrode. The use of a large number of individual filaments defining interstitial spaces among the filaments results in efficient and effective cooling of the brush electrode and of the tissue surface. The effective cooling of the brush electrode achieved by the present invention reduces the formation of coagulum on the electrode, and the effective cooling of the tissue surface achieved by the present invention allows for the application of high-power RF energy for long durations, ultimately resulting in the formation of better lesions.

During use of a surgical device with a brush electrode as disclosed herein, the following operating parameters may be taken into account: the incidence angle between the brush electrode and the tissue, the stand-off distance between the brush electrode and the tissue, the power applied, the rate of fluid flow when present, and the duration of contact between the electrode and the tissue.

In one set of tests, Thunderon® filaments were used favorably in a wet-brush electrode having a circular cross section with an overall diameter of 6-8 french, a tip length of 2-3 millimeters, and electrical resistance of 100-150 ohms. In this embodiment, the size of the Thunderon® filaments was 40 decitex. When using this brush electrode with zero stand-off distance, 30 watts of power, saline flowing at 12 milliliters per minute, and contact between the wet-brush electrode and the tissue occurring for 60 seconds, 5-to-6 millimeter deep lesions were formed with an incidence angle of 90° between the wet-brush electrode and the tissue. Four millimeter deep lesions were formed when the incidence angle between the wet-brush electrode and the tissue was 0°. When a stand-off distance of 1 millimeter was used during tests with similar operating parameters, a slightly less deep (on the order of 3 millimeters deep) lesion was formed.

In another set of tests, lesions 3-13 millimeters deep were created using 20-50 watts of power and fluid flow rates of 3-18 milliliters per minute with wet-brush electrodes made from commercially available carbon fibers (e.g., carbon fibers available through Cytec Carbon Fibers LLC of South Carolina, United States of America). Isotonic saline infusion was used in these tests. (Isotonic saline is generally about twice as conductive as blood.) In other tests, linear lesions 20-42 millimeters long and 3-8 millimeters deep were created by applying 20-50 watts of power for 60 seconds in the presence of flow rates of 3-18 milliliters per minute using wet-brush electrodes produced with conductive filaments made from Thunderon®.

As already mentioned, when conductive fluid is used, the brush electrode becomes a wet-brush electrode. In a wet-brush electrode, the conductive fluid serves both thermodynamic functions and electrical functions. Thermodynamically, the conductive fluid cools both the electrode and the tissue surface. As previously mentioned, effective cooling of the electrode inhibits or prevents coagulum formation on the electrode in blood-filled environments; and effective cooling of the tissue surface permits longer application of relatively high RF energy, resulting in the formation of the deeper lesions. Electrically, the conductive fluid serves as a virtual electrode. The conductive fluid also insulates the conductive brush filaments from the surrounding blood in blood-filled environments, which helps prevent the formation of coagulum. The conductive fluid also creates a conductivity gradient resulting from a concentration gradient. The conductive fluid flowing interstitially through the brush filaments has a field homogenizing effect. The conductive fluid flowing through the working surface at the distal tip of the wet-brush electrode thus helps to mitigate hot spots resulting from edge effects. Further, since the number of edges present in a brush electrode greatly exceeds the number of edges present in many existing electrodes, the energy build up at each filament edge in a brush electrode is less than it would be for existing electrodes, assuming the same power setting. This results in less severe edge effects when using the surgical device of the present invention. The conductive fluid, when used, further smoothes or reduces the undesirable edge effects.

In the surgical device of the present invention, the filaments of the wet-brush electrode serve both mechanical and electrical functions. Mechanically, the filaments create a flexible electrode that provides improved tissue contact. The filaments also create interstitial spaces, which not only provide effective fluid channeling, but also prevents the "virtual electrode" from being washed away by the surrounding blood in blood-filled environments, and helps to smooth the concentration gradient of the conductive fluid. Electrically, the filaments serve as a conductive electrode.

Again, it should be noted that although the filaments are depicted in nearly all of the figures as having circular cross-sections for simplicity, the individual filaments may intentionally or unintentionally have a wide variety of cross-sectional configurations and areas, and need not be circular. Manufacturing irregularities may result in various cross-sectional configurations, or filaments having a variety of different cross-sectional configurations may be intentionally selected to achieve a desired electric field at the brush-tissue interface. The number of filaments in the bundles of filaments of the brush electrodes depicted in the figures herein are meant to be representative only and are reflective of the limitations of line drawings. It should be recognized that a bundle of filaments may be composed of hundreds, thousands, or (in the case of carbon fibers, for example) tens of thousands of individual filaments. This provides an enormous increase in the surface area contact between the brush electrode and the tissue as compared to prior electrodes resulting in faster and improved energy transfer to the tissue. Reduction in the time of electrode-tissue contact reduces heat generated and thereby reduces the risk of tissue charring. The filaments also may not be perfectly aligned longitudinally. Further, the filaments may comprise a yarn of braided or twisted groups of fibers, or the filaments may comprise a roving pattern of untwisted, longitudinally-extending, substantially-parallel, conductive and nonconductive fibers.

Although various embodiments of this invention have been described above with a certain degree of particularity, or with reference to one or more individual embodiments, those skilled in the art could make numerous alterations to the disclosed embodiments without departing from the spirit or scope of this invention. It is intended that all matter contained in the above description and shown in the accompanying drawings shall be interpreted as illustrative only of particular embodiments and not limiting. All directional references (e.g., proximal, distal, upper, lower, upward, downward, left, right, lateral, front, back, top, bottom, above, below, vertical, horizontal, clockwise, and counter-clockwise) are only used for identification purposes to aid the reader's understanding of the present invention, and do not create limitations, particularly as to the position, orientation, or use of the invention. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the basic elements of the invention as defined in the following claims.

What is claimed is:

1. A surgical pencil for surgical treatment of tissue, said surgical pencil comprising
    a shaft having a distal end;
    a brush electrode, said brush electrode comprising
        a plurality of flexible filaments that directly or indirectly transfer therapeutic energy to target tissue, wherein said flexible filaments extend from said distal end of said shaft and each of said flexible filaments has a distal tip;
    a conductor in electrical contact with said plurality of flexible filaments;
    a fastener for securing said brush electrode to said distal end of said shaft; and
    an energy transfer coil surrounding at least a proximal portion of said brush electrode, wherein said conductor is electrically coupled with said energy transfer coil to transfer said therapeutic energy to said plurality of flexible filaments.

2. The surgical pencil of claim 1, wherein said distal tips of said plurality of flexible filaments are trimmed to create a shaped working surface of said brush electrode, and wherein said shaped working surface is selected from the group consisting of a relatively flat surface, a blade, a point, a cone, a trough, an arch, a dome, bowl, and a channel.

3. The surgical pencil of claim 1, wherein said brush electrode comprises said plurality of flexible filaments arranged in a bundle that is folded and inserted at least partly into a lumen in said distal end of said shaft.

4. The surgical pencil of claim 1, wherein at least some of said flexible filaments comprises tapered filaments.

5. The surgical pencil of claim 1, wherein said shaft provides mechanical support for said plurality of flexible filaments and provides electrical shielding for said plurality of flexible filaments.

6. The surgical pencil of claim 5, wherein at said distal end of said shaft, said tapered filaments have larger cross-sectional areas than said tapered filaments have at said distal tips of said tapered filaments.

7. The surgical pencil of claim 1, wherein said flexible filaments are selected from the group consisting of acrylic fibers, metal fibers, metal plated fibers, conductively-coated fibers, carbon fibers, and carbon-compound fibers.

8. The surgical pencil of claim 1, wherein said brush electrode further comprises a lead, wherein a distal end of said lead is embedded within said plurality of flexible filaments.

9. The surgical pencil of claim 1, wherein
said shaft comprises a threaded outer surface at said distal end;
said shaft further defines a lumen; said brush electrode comprises an exposed portion and an embedded portion; and
said embedded portion resides in said lumen at said distal end of said shaft; and wherein
said surgical pencil further comprises a cover surrounding said threaded outer surface of said shaft,
whereby a helical flow channel is defined between said threaded outer surface and said cover and transports fluid to said exposed portion of said brush electrode.

10. The surgical pencil of claim 1, wherein
said shaft comprises a grooved outer surface including at least one longitudinally-extending groove;
said shaft further defines a lumen;
said brush electrode comprises an exposed portion and an embedded portion; and
said embedded portion resides in said lumen at said distal end of said shaft; and wherein
said surgical pencil further comprises a cover surrounding said grooved outer surface of said shaft,
whereby at least one longitudinally-extending flow channel is defined between said grooved outer surface and said cover and transports fluid to said exposed portion of said brush electrode.

11. The surgical pencil of claim 1, wherein at least a first portion of said plurality of flexible filaments of said brush electrode comprises conductive materials.

12. The surgical pencil of claim 11, wherein each filament in said first portion of said plurality of flexible filaments has a longitudinal axis, and wherein each filament in said first portion has varying conductivity along said longitudinal axis.

13. The surgical pencil of claim 12 wherein at least a second portion of said plurality of flexible filaments of said brush electrode comprises nonconductive materials, and each filament in said second portion is longer than each filament in said first portion.

14. The surgical pencil of claim 11, wherein said distal tips of said first portion of said plurality of flexible filaments are nonconductive tips.

15. The surgical pencil of claim 1, wherein said shaft further defines a lumen that transports a fluid from a fluid source to said brush electrode.

16. The surgical pencil of claim 15, wherein said fluid is a conductive fluid.

17. The surgical pencil of claim 15, wherein interstitial gaps are defined among said plurality of flexible filaments and said fluid flows through said interstitial gaps to reach said distal tips.

18. The surgical pencil of claim 15, wherein at least a portion of said plurality of flexible filaments comprises hollow filaments.

19. The surgical pencil of claim 15, wherein at least a portion of said plurality of flexible filaments comprises porous filaments.

20. The surgical pencil of claim 15, wherein said brush electrode further comprises a device operatively connected to said lead and embedded among said plurality of flexible filaments.

21. The surgical pencil of claim 20, wherein said device is selected from the group consisting of a thermal sensor, a pressure sensor, and an ultrasound sensor.

22. The surgical pencil of claim 15, wherein said conductor extends within said lumen of said shaft.

23. The surgical pencil of claim 15, wherein
said brush electrode comprises an exposed portion and an embedded portion;
said shaft further comprises a plurality of tubes arranged in a circumferential ring around said lumen;
said embedded portion resides in said lumen at said distal end of said shaft; and
said plurality of tubes transport said fluid to said exposed portion of said brush electrode.

24. The surgical pencil of claim 16 further comprising
a porous inner sheath residing within said lumen, defining an inner lumen, and extending to said distal end of said shaft, and wherein
said brush electrode comprises an exposed portion and an embedded portion;
said embedded portion resides in said inner lumen at said distal end of said shaft; and
said porous inner sheath transports said fluid to said exposed portion of said brush electrode.

25. A surgical device comprising
an outer shaft having a distal end;
an inner sheath having a distal end;
an annular channel defined between said outer shaft and said inner sheath, wherein said annular channel is provided to carry fluid;
a mechanical interface supported at least in part by said distal end of said inner sheath;
a brush electrode supported by said mechanical interface and provided to apply therapeutic energy to target tissue, wherein
said brush electrode comprises an embedded portion and an exposed portion, and
said exposed portion extends from said distal end of said outer shaft and comprises a working surface;
a conductor that carries therapeutic energy connected between an energy source and said brush electrode, wherein said conductor comprises an uninsulated portion in electrical contact with said brush electrode; and
a flexible boot at said distal end of said outer shaft, said flexible boot defining an annular fluid jacket around a booted portion of said brush electrode, wherein
said booted portion comprises at least a portion of said exposed portion of said brush electrode, and
said annular fluid jacket is in fluid communication with said annular channel and carries fluid from said annular channel, and said booted portion directly contacting the brush electrode to direct the fluid to the brush electrode.

26. A surgical pencil for surgical treatment of tissue, said surgical pencil comprising
a shaft having a distal end;
a brush electrode, said brush electrode comprising
a plurality of flexible filaments that directly or indirectly transfer therapeutic energy to target tissue, wherein said flexible filaments extend from said distal end of said shaft and each of said flexible filaments has a distal tip;
a conductor in electrical contact with said plurality of flexible filaments;

a fastener for securing said brush electrode to said distal end of said shaft; and an energy transfer mesh surrounding at least a proximal portion of said brush electrode, wherein said conductor is electrically coupled with said energy transfer mesh to transfer said therapeutic energy to said plurality of flexible filaments.

* * * * *